US012629433B2

(12) United States Patent
Childress

(10) Patent No.: US 12,629,433 B2
(45) Date of Patent: May 19, 2026

(54) ULTRAVIOLET SANITIZING PACING SYSTEMS AND METHODS

(71) Applicant: THE BOEING COMPANY, Chicago, IL (US)

(72) Inventor: Jamie J. Childress, Mercer Island, WA (US)

(73) Assignee: The Boeing Company, Arlington, VA (US)

( * ) Notice: Subject to any disclaimer, the term of this patent is extended or adjusted under 35 U.S.C. 154(b) by 963 days.

(21) Appl. No.: 17/020,942

(22) Filed: Sep. 15, 2020

(65) Prior Publication Data

US 2021/0386883 A1 Dec. 16, 2021

Related U.S. Application Data

(60) Provisional application No. 63/037,630, filed on Jun. 11, 2020.

(51) Int. Cl.
*A61L 2/10* (2006.01)
*A61L 103/75* (2026.01)

(52) U.S. Cl.
CPC ............ *A61L 2/10* (2013.01); *A61L 2103/75* (2026.01); *A61L 2202/11* (2013.01); *A61L 2202/123* (2013.01); *A61L 2202/14* (2013.01); *A61L 2202/15* (2013.01); *A61L 2202/16* (2013.01)

(58) Field of Classification Search
CPC .. A61L 2/10; A61L 2202/11; A61L 2202/123; A61L 2202/14; A61L 2202/15; A61L 2202/16; A61L 2202/25; A61L 2/24; A61L 2/26
See application file for complete search history.

(56) References Cited

U.S. PATENT DOCUMENTS

| | | | |
|---|---|---|---|
| 10,232,954 B2 | 3/2019 | Siegmeth et al. | |
| 10,363,329 B2 | 7/2019 | Childress et al. | |
| 10,874,756 B1 * | 12/2020 | Guerrero | A61L 2/28 |
| 11,007,292 B1 * | 5/2021 | Grenon | A61L 2/24 |
| 11,058,785 B1 * | 7/2021 | Spurling | A61L 2/10 |
| 2008/0260601 A1 * | 10/2008 | Lyon | B01D 53/007 |
| | | | 422/186.3 |

(Continued)

FOREIGN PATENT DOCUMENTS

| | | |
|---|---|---|
| CN | 110167605 | 8/2019 |
| EP | 3522238 | 7/2019 |

(Continued)

OTHER PUBLICATIONS

U.S. Appl. No. 62/992,052, filed 2020.*

(Continued)

*Primary Examiner* — Regina M Yoo
(74) *Attorney, Agent, or Firm* — Joseph M. Butscher; Carroll, Hoette & Butscher, LLC

(57) ABSTRACT

An ultraviolet (UV) light pacing system includes a wand assembly including a UV lamp that is configured to emit UV light. A user device is configured to allow a user to select an item to be disinfected with the UV light. A pacing control unit is in communication with the user device. The pacing control unit is configured to output a pacing signal to the user device. The pacing signal includes pacing information regarding operation of the wand assembly to disinfect the item.

25 Claims, 16 Drawing Sheets

(56) References Cited

U.S. PATENT DOCUMENTS

| | | | |
|---|---|---|---|
| 2010/0044582 A1 | 2/2010 | Cooper | |
| 2011/0243789 A1* | 10/2011 | Roberts | A61L 2/10 |
| | | | 422/116 |
| 2015/0359915 A1 | 12/2015 | Farren | |
| 2016/0106873 A1* | 4/2016 | Dobrinsky | G01N 21/6456 |
| | | | 250/393 |
| 2017/0157276 A1 | 6/2017 | Dobrinsky | |
| 2017/0216466 A1 | 8/2017 | Dujowich | |
| 2017/0266330 A1 | 9/2017 | Liao | |
| 2018/0117191 A1* | 5/2018 | Shell | B65B 55/02 |
| 2018/0117194 A1* | 5/2018 | Dobrinsky | G01N 21/6486 |
| 2019/0030195 A1 | 1/2019 | Hatti | |
| 2019/0030196 A1* | 1/2019 | Bilenko | A61L 2/10 |
| 2019/0255201 A1 | 8/2019 | Rosen | |
| 2021/0299316 A1* | 9/2021 | Mullen | A61L 2/26 |
| 2021/0346561 A1* | 11/2021 | Callahan | A61L 2/28 |
| 2021/0358621 A1* | 11/2021 | Castle | A61B 5/01 |
| 2022/0016281 A1* | 1/2022 | Eigner | A61L 2/24 |

FOREIGN PATENT DOCUMENTS

| | | |
|---|---|---|
| EP | 3915592 | 1/2021 |
| JP | 2017-124220 | 7/2017 |
| JP | 2020-511344 | 4/2020 |
| WO | WO 2013/106077 | 7/2013 |
| WO | WO 2017/020028 | 2/2017 |
| WO | 2019008227 | 1/2019 |
| WO | WO 2019/164810 | 8/2019 |
| WO | WO 2019/190967 | 10/2019 |

OTHER PUBLICATIONS

U.S. Appl. No. 17/016,466, filed Sep. 10, 2020.
U.S. Appl. No. 29/735,235, filed May 19, 2020.
U.S. Appl. No. 17/039,011, filed Sep. 30, 2020.
U.S. Appl. No. 17/026,414, filed Sep. 21, 2020.
U.S. Appl. No. 16/987,514, filed Aug. 7, 2020.
U.S. Appl. No. 17/104,628, filed Nov. 25, 2020.
U.S. Appl. No. 16/987,647, filed Aug. 7, 2020.
U.S. Appl. No. 17/026,417, filed Sep. 21, 2020.
U.S. Appl. No. 17/020,951, filed Sep. 15, 2020.
"Honeywell UV Treatment System," https://aerospace.honeywell.com/en/learn/products/cabin/uv-cabin-system.
U.S. Appl. No. 17/026,435, filed Sep. 21, 2020.
U.S. Appl. No. 17/022,392, filed Sep. 16, 2020.
Extended European Search Report for EP 21178864.1-1202, dated Nov. 5, 2021.
Extended European Search Report for EP 21172799.5, dated Nov. 26, 2021.
Communication re EP 21178864.1-1201, dated Apr. 5, 2023.
Communication pursuant to Article 94(3) EPC for EP 21178864.1-1201, dated Feb. 20, 2024.

\* cited by examiner

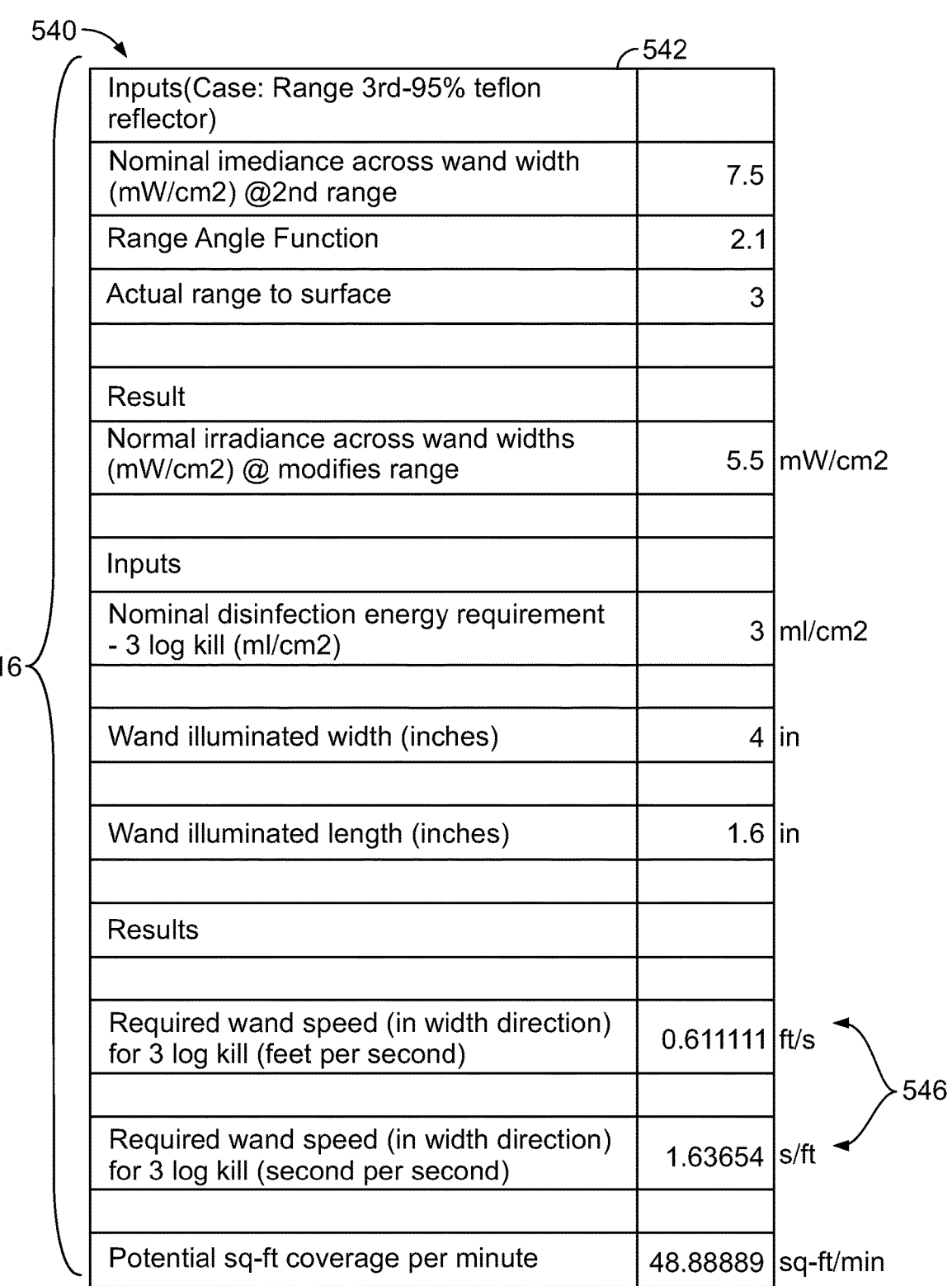

| Inputs(Case: Range 3rd-95% teflon reflector) | | |
|---|---|---|
| Nominal imediance across wand width (mW/cm2) @2nd range | 7.5 | |
| Range Angle Function | 2.1 | |
| Actual range to surface | 3 | |
| | | |
| Result | | |
| Normal irradiance across wand widths (mW/cm2) @ modifies range | 5.5 | mW/cm2 |
| | | |
| Inputs | | |
| Nominal disinfection energy requirement - 3 log kill (ml/cm2) | 3 | ml/cm2 |
| | | |
| Wand illuminated width (inches) | 4 | in |
| | | |
| Wand illuminated length (inches) | 1.6 | in |
| | | |
| Results | | |
| | | |
| Required wand speed (in width direction) for 3 log kill (feet per second) | 0.611111 | ft/s |
| | | |
| Required wand speed (in width direction) for 3 log kill (second per second) | 1.63654 | s/ft |
| | | |
| Potential sq-ft coverage per minute | 48.88889 | sq-ft/min |

FIG. 27

ULTRAVIOLET SANITIZING PACING SYSTEMS AND METHODS

RELATED APPLICATIONS

This application relates to and claims priority benefits from U.S. Provisional Patent Application No. 63/037,630, entitled "Ultraviolet Sanitizing Pacing Systems and Methods," filed Jun. 11, 2020.

FIELD OF THE DISCLOSURE

Embodiments of the present disclosure generally relate to sanitizing systems, such as may be used to sanitize structures and areas within vehicles, and more particularly to systems and methods of pacing movement of such sanitizing systems.

BACKGROUND OF THE DISCLOSURE

Vehicles such as commercial aircraft are used to transport passengers between various locations. Systems are currently being developed to disinfect or otherwise sanitize surfaces within aircraft, for example, that use ultraviolet (UV) light. In order to sanitize a surface of a structure, a known UV light sterilization method emits a broad spectrum UVC light onto the structure.

Further, known UV light sanitizing systems are typically large, bulky, and often require fixed, stationary infrastructure.

SUMMARY OF THE DISCLOSURE

A need exists for a system and a method for efficiently sterilizing surfaces within an internal cabin of a vehicle. Further, a need exists for a mobile, compact, easy-to-use, and safe system and method for using UV light to sterilize surfaces within an internal cabin.

With those needs in mind, certain embodiments of the present disclosure provide an ultraviolet (UV) light pacing system including a wand assembly including a UV lamp that is configured to emit UV light. A user device is configured to allow a user to select an item to be disinfected with the UV light. A pacing control unit is in communication with the user device. The pacing control unit is configured to output a pacing signal to the user device. The pacing signal includes pacing information regarding operation of the wand assembly to disinfect the item.

In at least one embodiment, the pacing information includes instructions for operating the wand assembly to disinfect the item. The instructions are shown on a display of the user device.

In at least one embodiment, the pacing information includes one or more audio cues for pacing motion of the wand assembly during a disinfection process of the item. The one or more audio cues are broadcast by a speaker of the user device.

In at least one embodiment, the user device is a handheld device. The user device may include the pacing control unit.

In at least one embodiment, the UV light pacing system also includes a pacing database that stores pacing data regarding the item. The pacing control unit is in communication with the pacing database. The pacing control unit is configured to determine the pacing information from the pacing data. The user device may include the pacing database.

In at least one embodiment, the user device includes a display. The pacing control unit is configured to show a pacing menu screen on the display. The pacing menu screen may include one or more training options.

In at least one embodiment, the pacing information includes wand movement speed.

Examples of the item include a passenger seat, a monument, a stowage bin assembly, a component within a lavatory, a component within a galley, a component within a flight deck, or the like.

In at least one embodiment, the UV lamp is configured to emit the UV light having a wavelength between 200 nm-230 nm. For example, the UV lamp is configured to emit the UV light having a wavelength of 222 nm.

In at least one other embodiment, the UV lamp is configured to emit the UV light having a wavelength of 230 nm-280 nm. For example, the UV lamp is configured to emit the UV light having a wavelength of 254 nm.

Certain embodiments of the present disclosure provide an ultraviolet (UV) light pacing method, including using a wand assembly including a UV lamp to emit UV light; selecting, by a user device. an item to be disinfected with the UV light; and outputting, from a pacing control unit in communication with the user device, a pacing signal to the user device. The pacing signal includes pacing information regarding operation of the wand assembly to disinfect the item.

In at least one embodiment, the pacing information includes instructions for operating the wand assembly to disinfect the item. The method further includes showing the instructions on a display of the user device.

In at least one embodiment, the pacing information includes one or more audio cues for pacing motion of the wand assembly during a disinfection process of the item. The method further includes broadcasting the one or more audio cues by a speaker of the user device.

In at least one embodiment, the UV light pacing method also includes storing, in a pacing database, pacing data regarding the item; communicatively coupling the pacing control unit with the pacing database; and determining, by the pacing control unit, the pacing information from the pacing data.

BRIEF DESCRIPTION OF THE DRAWINGS

FIG. 27 illustrates a spreadsheet of pacing information, according to an embodiment of the present disclosure.

DETAILED DESCRIPTION OF THE DISCLOSURE

Figure 1:
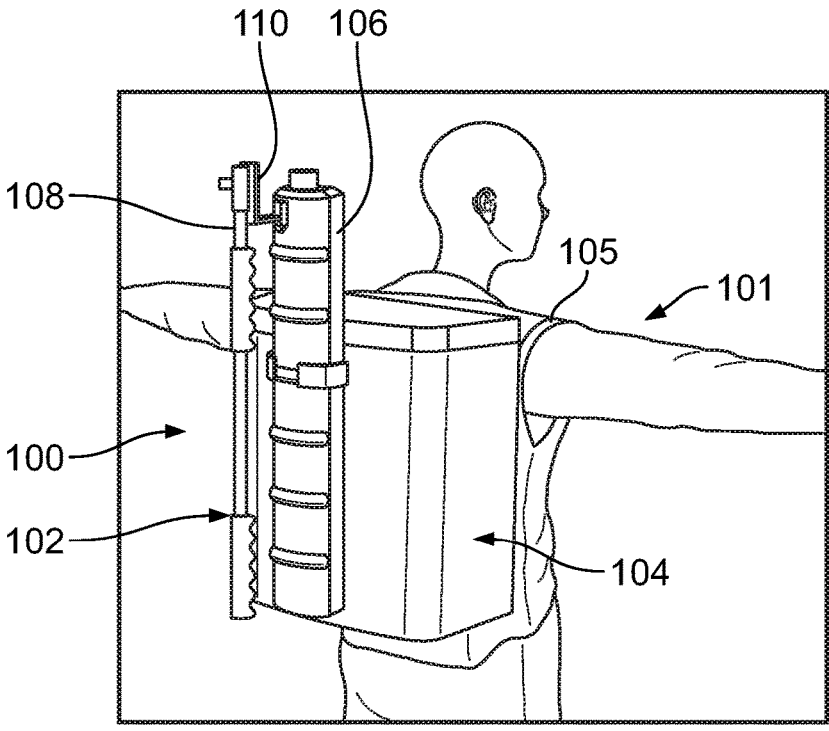
FIG. 1 illustrates a perspective view of a portable sanitizing system worn by an individual, according to an embodiment of the present disclosure.

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps.

Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular condition can include additional elements not having that condition.

Certain embodiments of the present disclosure provide a portable sanitizing system for disinfecting surfaces, such as within an internal cabin of a vehicle. The portable sanitizing system includes a wand assembly and a backpack assembly. The wand assembly includes a housing, a UV lamp, a reflector, mounts to secure the UV lamp to the housing, an inlet to allow air to be drawn across the UV lamp, and an extension handle that is configured to extend a reach of the wand assembly. The backpack assembly includes a main body or housing, a power supply, one or more batteries (such as rechargeable batteries), a plug for recharging the backpack, an air blower, a carbon filter, an exhaust vent, and a harness to allow an individual to wear the portable sanitizing system.

The effectiveness of a UV sanitation system is determined by a dose (such as in $mJ/cm^2$) required to kill a targeted pathogen. The dose is a function of an optical power of the UV light (in watts) and the time of exposure. Embodiments of the present disclosure provide a training and pacing audio system that provides a user with a cue (such as an audio cue) allowing them to provide a correct amount of time for sanitizing UV light exposure. Embodiments of the present disclosure allow a user to pace movement of a wand assembly during sanitation to ensure that a correct dose of UV light for disinfecting has been delivered. Embodiments of the present disclosure guide the user according to a required irradiation dose and/or a specific item or items being sanitized.

Certain embodiments of the present disclosure provide a method of pacing UV disinfection of a predetermined surface. The method includes calculating a wand speed, and loading the speed into a computer program. The program provides audio cues regarding a rate at which to move the wand, and may provide feedback so that the user can maintain said rate.

The audio cues may be a series of audio files to provide voice instruction and pacing for the area to be cleaned, or may include a tone such as a metronome beat and and/or cymbal sounds to indicate the end of the sweep period. The audio files may be loaded into a computer program, such as a mobile app, to act as an audio coach to instruct the user how long to hold the UV wand over the area to disinfect. The computer program may include a mobile app or other computer program to manage the audio files.

The wand speed is calculated by entering known parameters such as range to surface, irradiance of wand, disinfection energy required to sanitize the surface, wand length, and wand width to conduct calculations for time required to disinfect surfaces.

FIG. 1 illustrates a perspective view of a portable sanitizing system 100 worn by an individual 101, according to an embodiment of the present disclosure. The portable sanitizing system 100 includes a wand assembly 102 coupled to a backpack assembly 104 that is removably secured to the individual through a harness 105. The wand assembly 102 includes a sanitizing head 106 coupled to a handle 108. In at least one embodiment, the sanitizing head 106 is moveably coupled to the handle 108 through a coupler 110.

As shown in FIG. 1, the wand assembly 102 is in a stowed position. In the stowed position, the wand assembly 102 is removably secured to a portion of the backpack assembly 104, such as through one or more tracks, clips, latches, belts, ties, and/or the like.

Figure 2:
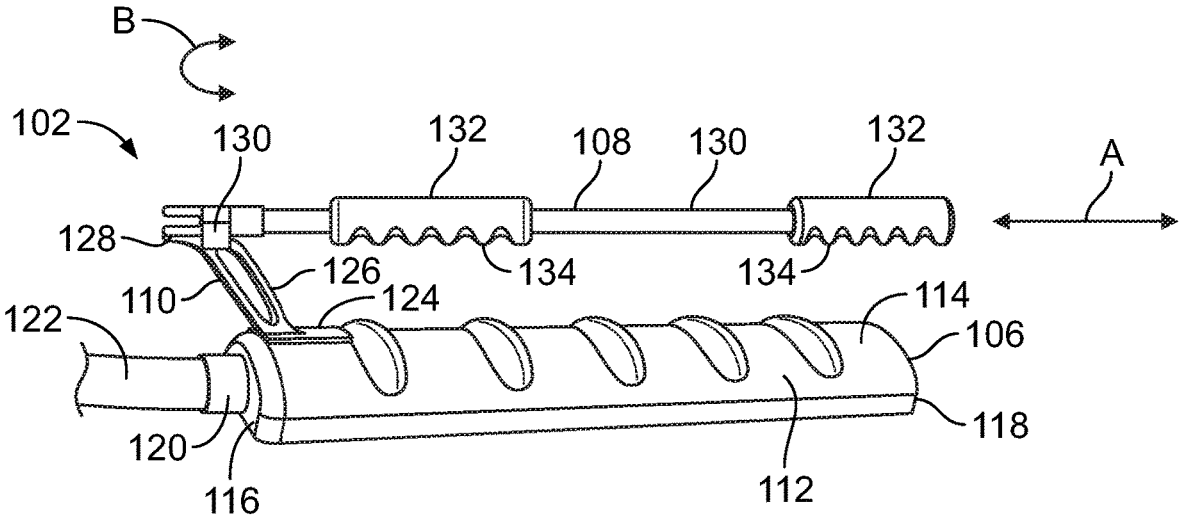
FIG. 2 illustrates a perspective lateral top view of a wand assembly, according to an embodiment of the present disclosure.

FIG. 2 illustrates a perspective lateral top view of the wand assembly 102, according to an embodiment of the present disclosure. The sanitizing head 106 couples to the handle 108 through the coupler 110. The sanitizing head 106 includes a shroud 112 having an outer cover 114 that extends from a proximal end 116 to a distal end 118. As described herein, the shroud 112 contains a UV lamp.

A port 120 extends from the proximal end 116. The port 120 couples to a hose 122, which, in turn, couples to the backpack assembly 104 (shown in FIG. 1). The hose 122 contains electrical cords, cables, wiring, or the like that couples a power source or supply (such as one or more batteries) within the backpack assembly 104 (shown in FIG. 1) to a UV lamp 140 within the shroud 112. Optionally, the electrical cords, cables, wiring, or the like may be outside of the hose 122. The hose 122 also contains an air delivery line, such as an air tube) that fluidly couples an internal chamber of the shroud 112 to an air blower, vacuum generator, air filters, and/or the like within the backpack assembly 104.

The coupler 110 is secured to the outer cover 114 of the shroud 112, such as proximate to the proximal end 116. The coupler 110 may include a securing beam 124 secured to the outer cover 114, such as through one or more fasteners, adhesives, and/or the like. An extension beam 126 outwardly extends from the securing beam 124, thereby spacing the handle 108 from the shroud 112. A bearing assembly 128 extends from the extension beam 126 opposite from the securing beam 124. The bearing assembly 128 includes one or more bearings, tracks, and/or the like, which allow the handle 108 to linearly translate relative to the coupler 110 in the directions of arrows A, and/or pivot about a pivot axle in the directions of arc B. Optionally, the securing beam 124 may include a bearing assembly that allows the sanitizing head 106 to translate in the directions of arrows A, and/or rotate (for example, swivel) in the directions of arc B in addition to, or in place of, the handle 108 being coupled to the bearing assembly 128 (for example, the handle 108 may be fixed to the coupler 110).

In at least one embodiment, the handle 108 includes a rod, pole, beam, or the like 130, which may be longer than the shroud 112. Optionally, the rod 130 may be shorter than the shroud 112. One or more grips 132 are secured to the rod 130. The grips 132 are configured to be grasped and held by an individual. The grips 132 may include ergonomic tactile features 134.

Optionally, the wand assembly 102 may be sized and shaped differently than shown. For example, in at least one embodiment, the handle 108 may be fixed in relation to the shroud 112. Further, the handle 108 may or may not be configured to move relative to itself and/or the shroud 112. For example, the handle 108 and the shroud 112 may be integrally molded and formed as a single unit.

In at least one embodiment, the wand assembly 102 is not coupled to a backpack assembly. For example, the wand assembly 102 is a standalone unit having a power source, such as one or more batteries. As another example, the wand assembly 102 is coupled to a case assembly.

Figure 3:
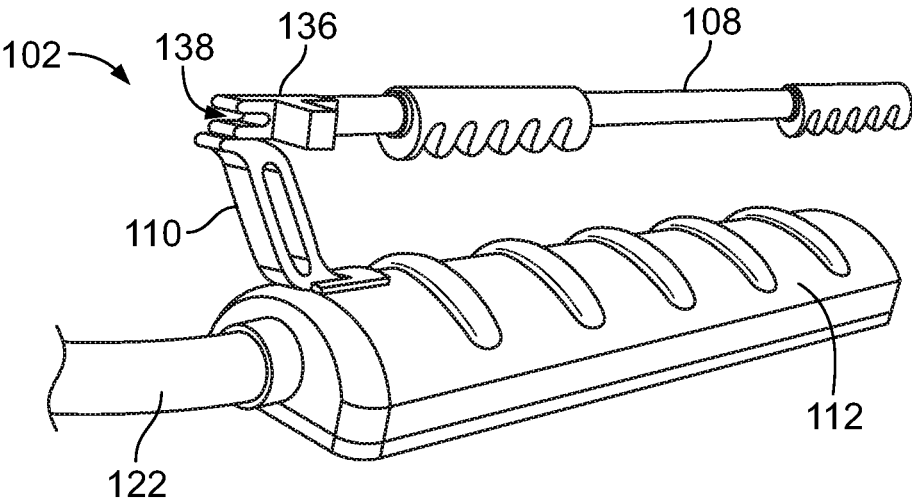
FIG. 3 illustrates a perspective rear view of the wand assembly of FIG. 2.
Figure 4:
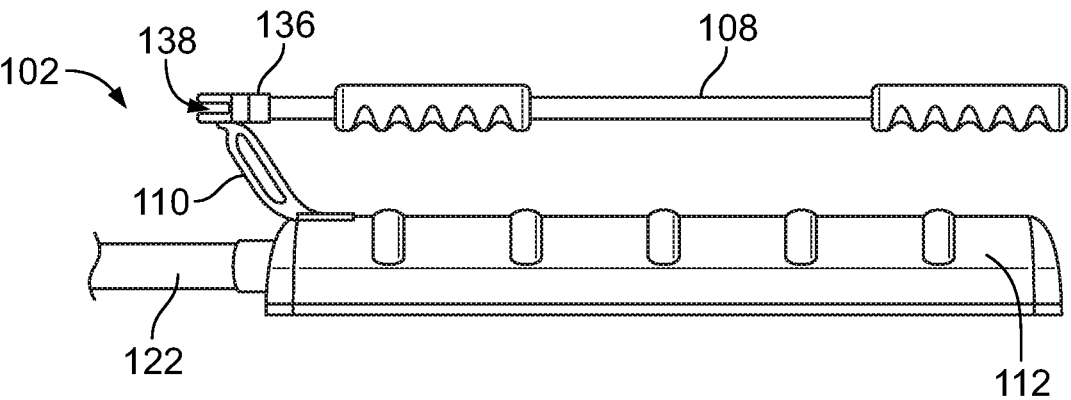
FIG. 4 illustrates a perspective lateral view of the wand assembly of FIG. 2.

FIG. 3 illustrates a perspective rear view of the wand assembly 102 of FIG. 2. FIG. 4 illustrates a perspective lateral view of the wand assembly 102 of FIG. 2. Referring to FIGS. 3 and 4, the handle 108 may pivotally couple to the coupler 110 through a bearing 136 having a pivot axle 138 that pivotally couples the handle 108 to the coupler 110. The handle 108 may further be configured to linearly translate into and out of the bearing 136. For example, the handle 108 may be configured to telescope in and out. Optionally, or alternatively, in at least one embodiment, the handle 108 may include a telescoping body that allows the handle 108 to outwardly extend and inwardly recede.

Figure 5:
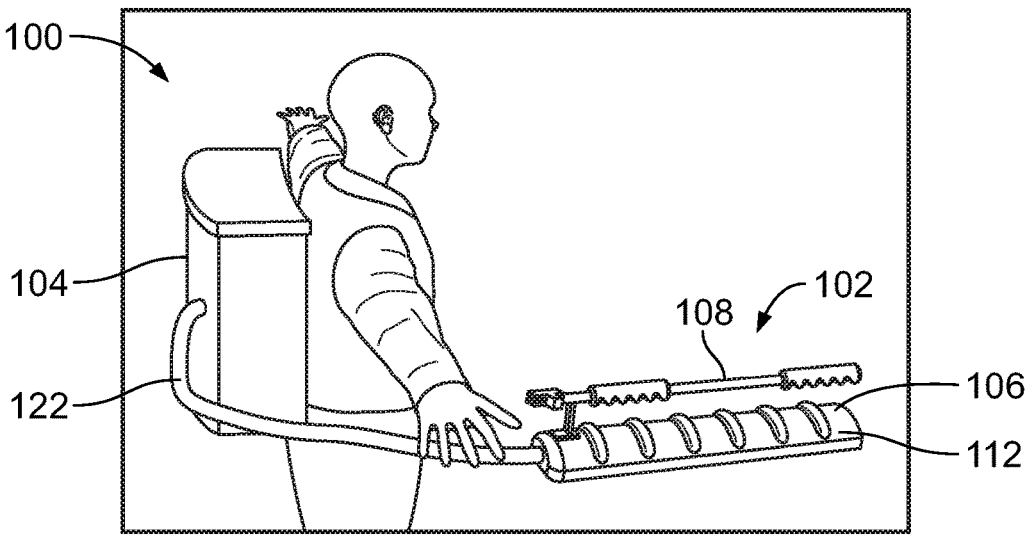
FIG. 5 illustrates a perspective view of the portable sanitizing system in a compact deployed position, according to an embodiment of the present disclosure.

FIG. 5 illustrates a perspective view of the portable sanitizing system 100 in a compact deployed position, according to an embodiment of the present disclosure. The wand assembly 102 is removed from the backpack assembly 104 (as shown in FIG. 1) into the compact deployed position, as shown in FIG. 5. The hose 122 connects the wand assembly 102 to the backpack assembly 104. In the compact deployed position, the sanitizing head 106 is fully retracted in relation to the handle 108.

Figure 6:
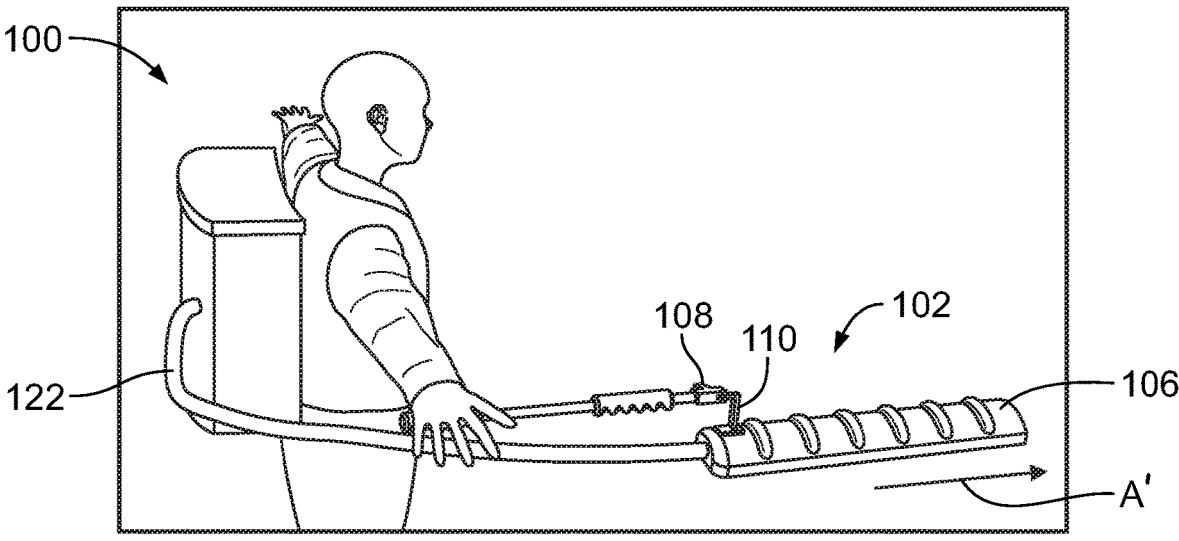
FIG. 6 illustrates a perspective view of the portable sanitizing system having a sanitizing head in an extended position, according to an embodiment of the present disclosure.

FIG. 6 illustrates a perspective view of the portable sanitizing system 100 having the sanitizing head 106 in an extended position, according to an embodiment of the present disclosure. In order to extend the sanitizing head 106 relative to the handle 108, the sanitizing head 106 is outwardly slid relative to the handle 108 in the direction of arrow A' (or the handle 108 is rearwardly slid relative to the sanitizing head 106). As noted, the sanitizing head 106 is able to linearly translate in the direction of arrow A' relative to the handle 108 via the coupler 110. The outward extension of the sanitizing head 106, as shown in FIG. 6, allows for the portable sanitizing system 100 to easily reach distant areas. Alternatively, the sanitizing head 106 may not linearly translate relative to the handle 108.

Figure 7:
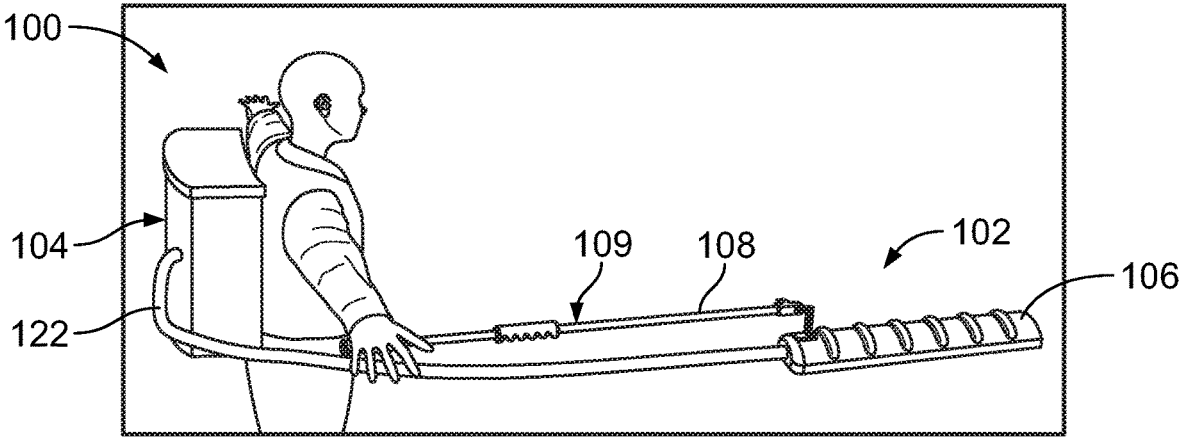
FIG. 7 illustrates a perspective view of the portable sanitizing system having the sanitizing head in an extended position and a handle in an extended position, according to an embodiment of the present disclosure.

FIG. 7 illustrates a perspective view of the portable sanitizing system 100 having the sanitizing head 106 in an extended position and the handle 108 in an extended position, according to an embodiment of the present disclosure. To reach even further, the handle 108 may be configured to linearly translate, such as through a telescoping portion, to allow the sanitizing head 106 to reach further outwardly. Alternatively, the handle 108 may not be configured to extend and retract.

In at least one embodiment, the handle 108 may include a lock 109. The lock 109 is configured to be selectively operated to secure the handle 108 into a desired extended (or retracted) position.

Figure 8:
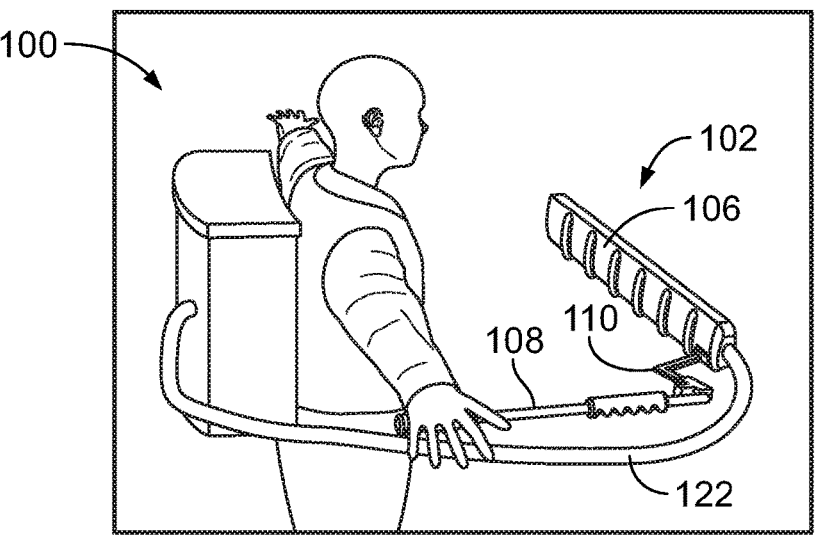
FIG. 8 illustrates a perspective view of the portable sanitizing system having the sanitizing head rotated in relation to the handle, according to an embodiment of the present disclosure.

FIG. 8 illustrates a perspective view of the portable sanitizing system 100 having the sanitizing head 106 rotated in relation to the handle 108, according to an embodiment of the present disclosure. As noted, the sanitizing head 106 is configured to rotate relative to the handle 108 via the coupler 110. Rotating the sanitizing head 106 relative to the handle 108 allows the sanitizing head 106 to be moved to a desired position, and sweep or otherwise reach into areas that would otherwise be difficult to reach if the sanitizing head 106 was rigidly fixed to the handle 108. Alternatively, the sanitizing head 106 may not be rotatable relative to the handle 108.

Figure 9:
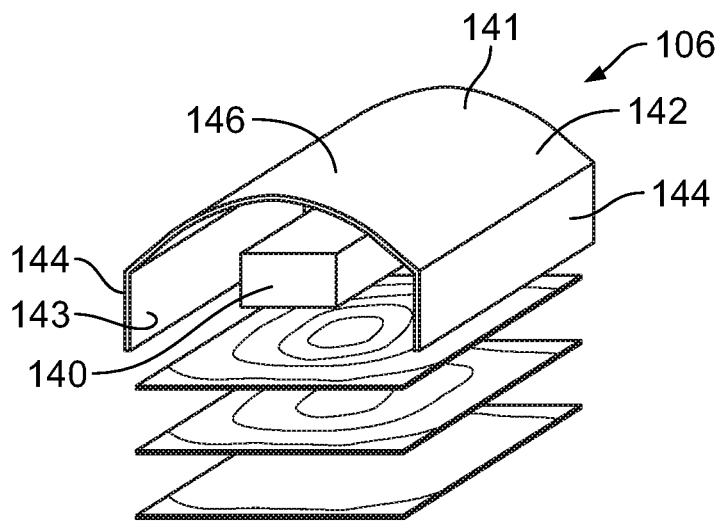
FIG. 9 illustrates a perspective end view of a UV lamp and a reflector of the sanitizing head, according to an embodiment of the present disclosure.

FIG. 9 illustrates a perspective end view of a UV lamp 140 and a reflector 142 of the sanitizing head 106, according to an embodiment of the present disclosure. The UV lamp 140 and the reflector 142 are secured within the shroud 112 (shown in FIG. 2, for example) of the sanitizing head 106. In at least one embodiment, the reflector 142 is secured to an underside 141 of the shroud 112, such as through one or more adhesives. As another example, the reflector 142 is an integral part of the shroud 112. For example, the reflector 142 may be or otherwise provide the underside 141 of the shroud 112. The reflector 142 provides a reflective surface 143 (such as formed of Teflon, a mirrored surface, and/or the like) that is configured to outwardly reflect UV light emitted by the UV lamp 140. In at least one example, shroud 112 may be or include a shell formed of fiberglass, and the reflector 142 may be formed of Teflon that provides a 98% reflectivity.

The reflector 142 may extend along an entire length of the underside 141 of the shroud 112. Optionally, the reflector 142 may extend along less than an entire length of the underside 141 of the shroud 112.

The UV lamp 140 may extend along an entire length (or along substantially the entire length, such as between the ends 116 and 118). The UV lamp 140 is secured to the reflector 142 and/or the shroud 112 through one or more brackets, for example. The UV lamp 140 includes one or more UV light emitters, such as one more bulbs, light emitting elements (such as light emitting diodes), and/or the like. In at least one embodiment, the UV lamp 140 is configured to emit UV light in the far UV spectrum, such as at a wavelength between 200 nm-230 nm. In at least one embodiment, the UV lamp 140 is configured to emit UV light having a wavelength of 222 nm. For example, the UV lamp 140 may be or include a 300 W bulb that is configured to emit UV light having a wavelength of 222 nm.

As shown, the reflector 142 includes flat, upright side walls 144 connected together through an upper curved wall 146. The upper curved wall 146 may be bowed outwardly away from the UV lamp 140. For example, the upper curved wall 146 may have a parabolic cross-section and/or profile.

It has been found that the straight, linear side walls 144 provide desired reflection and/or focusing of UV light emitted from the UV lamp 140 toward and onto a desired location. Alternatively, the side walls 144 may not be linear and flat.

Figure 10:
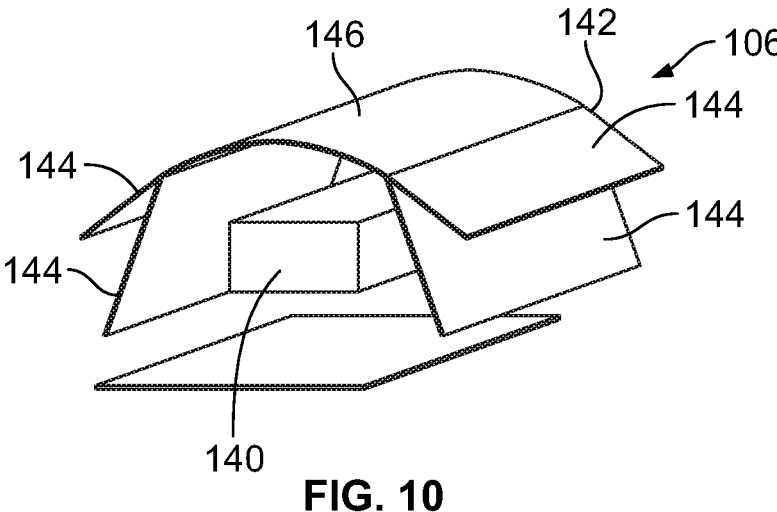
FIG. 10 illustrates a perspective end view of a UV lamp and a reflector of the sanitizing head, according to an embodiment of the present disclosure.

FIG. 10 illustrates a perspective end view of the UV lamp 140 and a reflector 142 of the sanitizing head, according to an embodiment of the present disclosure. The reflector 142 shown in FIG. 10 is similar to the reflector 142 shown in FIG. 9, except that the side walls 144 may outwardly cant from the upper curved wall 146.

Figure 11:
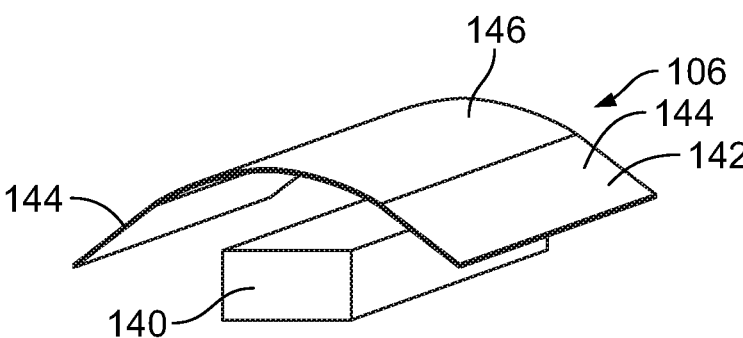
FIG. 11 illustrates a perspective end view of a UV lamp and a reflector of the sanitizing head, according to an embodiment of the present disclosure.

FIG. 11 illustrates a perspective end view of the UV lamp 140 and the reflector 142 of the sanitizing head, according to an embodiment of the present disclosure. In this embodiment, the side walls 144 may be curved according to the curvature of the upper curved wall 146.

Figure 12:
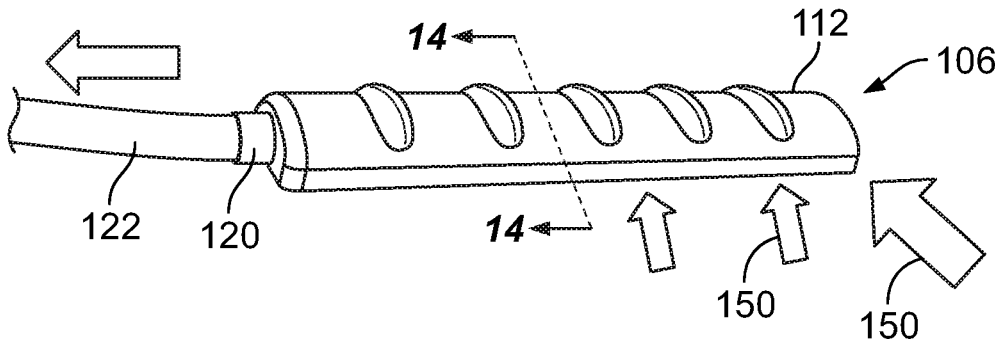
FIG. 12 illustrates a perspective top view of the sanitizing head.
Figure 13:
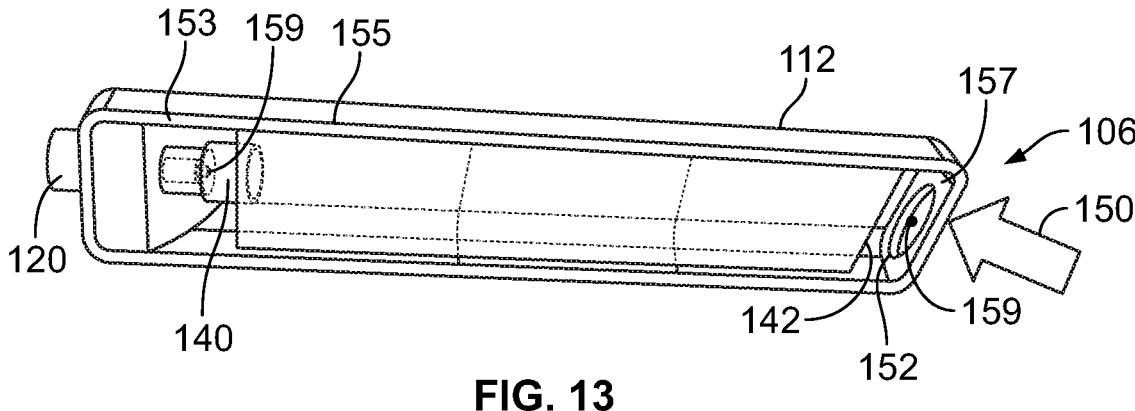
FIG. 13 illustrates a perspective bottom view of the sanitizing head.
Figure 14:
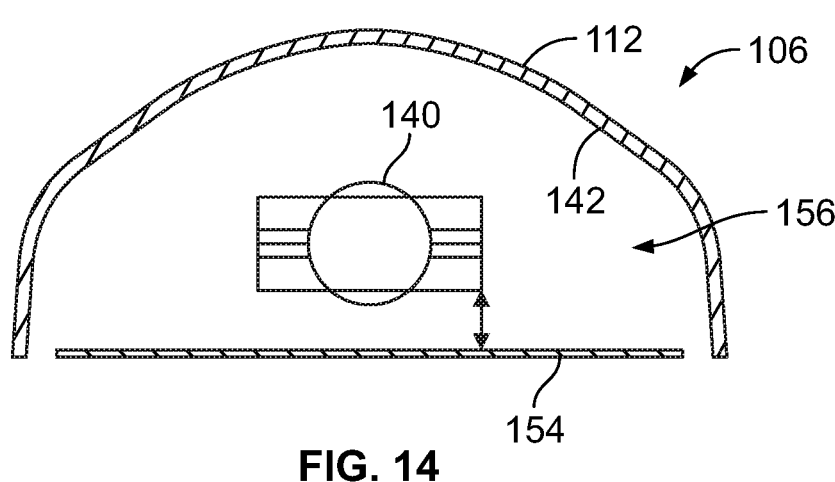
FIG. 14 illustrates an axial cross-sectional view of the sanitizing head through line 14-14 of FIG. 12.

FIG. 12 illustrates a perspective top view of the sanitizing head 106. FIG. 13 illustrates a perspective bottom view of the sanitizing head 106. FIG. 14 illustrates an axial cross-sectional view of the sanitizing head 106 through line 14-14 of FIG. 12. Referring to FIGS. 12-14, air 150 is configured to be drawn into the sanitizing head 106 through one or more openings 152 (or simply an open chamber) of the shroud 112. The air 150 is drawn into the sanitizing head 106, such as via a vacuum generator within the backpack assembly 104 (shown in FIG. 1). The air 150 is drawn into the shroud 112, and cools the UV lamp 140 as it passes over and around the UV lamp 140. The air 150 passes into the port 120 and into the hose 122, such as within an air tube within the hose 122. The air 150 not only cools the UV lamp 140, but also removes ozone, which may be generated by operation of the UV lamp 140, within the shroud 112. The air 150 may be drawn to an air filter, such as an activated carbon filter, within the backpack assembly 104.

In at least one embodiment, the portable sanitizing system 100 may also include an alternative ozone mitigation system. As an example, the ozone mitigation system may be disposed in the shroud 112 or another portion of the system, and may include an inert gas bath, or a face inert gas system, such as in U.S. Pat. No. 10,232,954.

Referring to FIG. 13, in particular, a bumper 153 may be secured to an exposed lower circumferential edge 155 of the shroud 112. The bumper 153 may be formed of a resilient material, such as rubber, another elastomeric material, open or closed cell foam, and/or the like. The bumper 153 protects the sanitizing head 106 from damage in case the sanitizing head 106 inadvertently contacts a surface. The bumper 153 also protects the surface from damage.

The openings 152 may be spaced around the lower surface of the shroud 112 such that they do not provide a direct view of the UV lamp 140. For example, the openings 152 may be positioned underneath portions that are spaced apart from the UV lamp 140.

Referring to FIG. 14, in particular, the sanitizing head 106 may include a cover plate 154 below the UV lamp 140. The cover plate 154 may be formed of glass, for example, and may be configured to filter UV light emitted by the UV lamp 140. The UV lamp 140 may be secured within an interior chamber 156 defined between the reflector 142 and the cover plate 154. In at least one embodiment, the cover plate 154 is or otherwise includes a far UV band pass filter. For example, the cover plate 154 may be a 222 nm band pass filter that filters UV light emitted by the UV lamp 140 to a 222 nm wavelength. As such, UV light that is emitted from the sanitizing head 106 may be emitted at a wavelength of 222 nm.

Referring to FIGS. 13 and 14, a rim 157 (such as a 0.020" thick Titanium rim) may connect the cover plate 154 to the shroud 112. The rim 157 may distribute impact loads therethrough and/or therearound.

In at least one embodiment, ranging light emitting diodes (LEDs) 159 may be disposed proximate to ends of the UV lamp 140. The ranging LEDs 159 may be used to determine a desired range to a structure that is to be sanitized, for example. In at least one embodiment, the ranging LEDs 159 may be disposed on or within the rim 157 and/or the cover plate 154.

Figure 15:
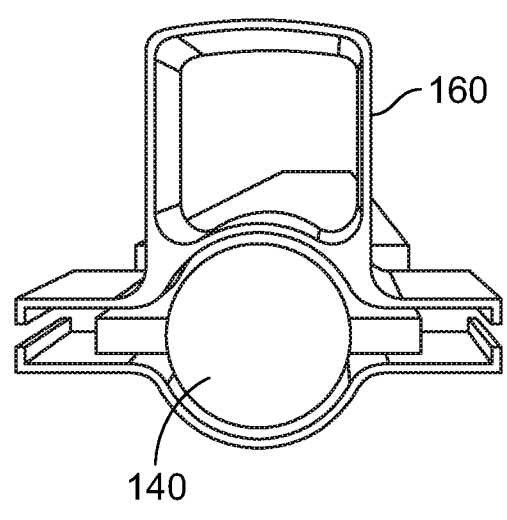
FIG. 15 illustrates a perspective end view of the UV lamp secured to a mounting bracket, according to an embodiment of the present disclosure.

FIG. 15 illustrates a perspective end view of the UV lamp 140 secured to a mounting bracket or clamp 160, according to an embodiment of the present disclosure. Each end of the UV lamp 140 may be coupled to mounting bracket or clamp 160, which secures the UV lamp 140 to the shroud 112 (shown in FIGS. 12-14). A buffer, such as a thin (for example, 0.040") sheet of silicon may be disposed between the end of the UV lamp 140 and the bracket 160. Optionally, the UV lamp 140 may be secured to the shroud 112 through brackets or clamps that differ in size and shape than shown. As another example, the UV lamp 140 may be secured to the shroud 112 through adhesives, fasteners, and/or the like.

Figure 16:
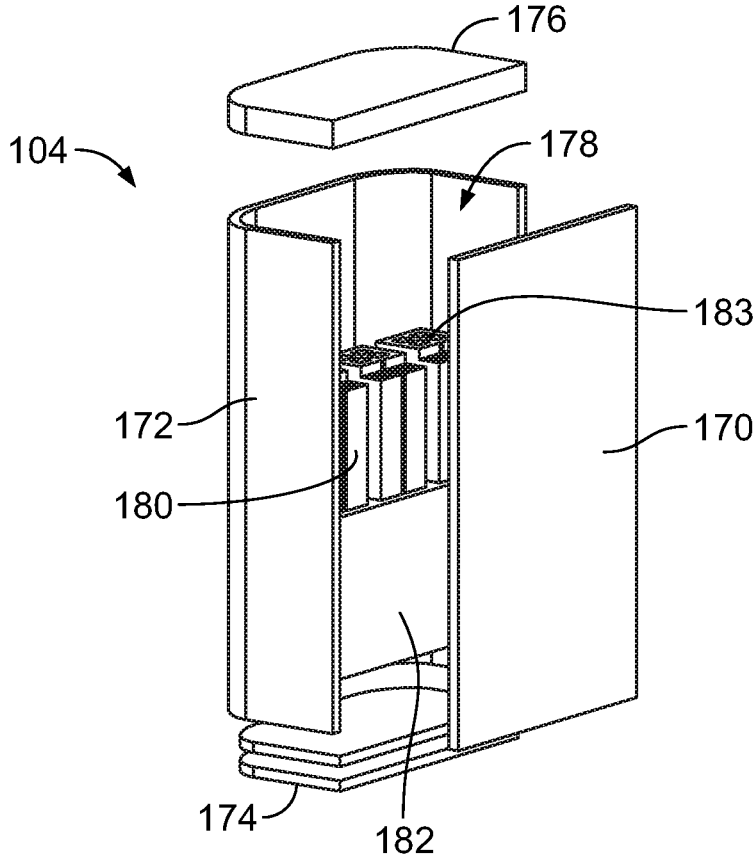
FIG. 16 illustrates a perspective exploded view of a backpack assembly, according to an embodiment of the present disclosure.

FIG. 16 illustrates a perspective exploded view of the backpack assembly 104, according to an embodiment of the present disclosure. The backpack assembly 104 includes a front wall 170 that couples to a rear shell 172, a base 174, and a top cap 176. An internal chamber 178 is defined between the front wall 170, the rear shell 172, the base 174, and the top cap 176. One or more batteries 180, such as rechargeable Lithium batteries, are contained within the internal chamber 178. An air generation sub-system 182 is also contained within the internal chamber 178. The air generation sub-system 182 is in fluid communication with an air tube within the hose 122 (shown in FIG. 2, for example). The air generation sub-system 182 may include an airflow device, such as a vacuum generator, an air blower, and/or the like. The airflow device is configured to generate airflow to cool the UV lamp, draw air from the sanitizing head 106 into the backpack assembly 104 and out through an exhaust, draw or otherwise remove generated ozone away from the shroud 112, and/or the like.

One or more air filters 183, such as carbon filters, are within the backpack assembly 104. The air filters 183 are in communication with the air tube or other such delivery duct or line that routes air through the hose 122 and into the backpack assembly 104. The air filters 183 are configured to filter the air that is drawn into the backpack assembly 104 from the shroud 112. For example, the air filters 183 may be configured to remove, deactivate, or otherwise neutralize ozone.

The batteries 180 and/or a power supply within the backpack assembly 104 provides operating power for the UV lamp 140 of the sanitizing head 106 (shown in FIG. 2, for example). The top wall 176 may be removably coupled to the front wall 170 and the rear shell 172. The top wall 176 may be removed to provide access to the batteries 180 (such as to remove and/or recharge the batteries), for example. Additional space may be provided within the backpack assembly 104 for storage of supplies, additional batteries, additional components, and/or the like. In at least one embodiment, the front wall 170, the rear shell 172, the base 174, and the top cap 176 may be formed of fiberglass epoxy.

Figure 17:
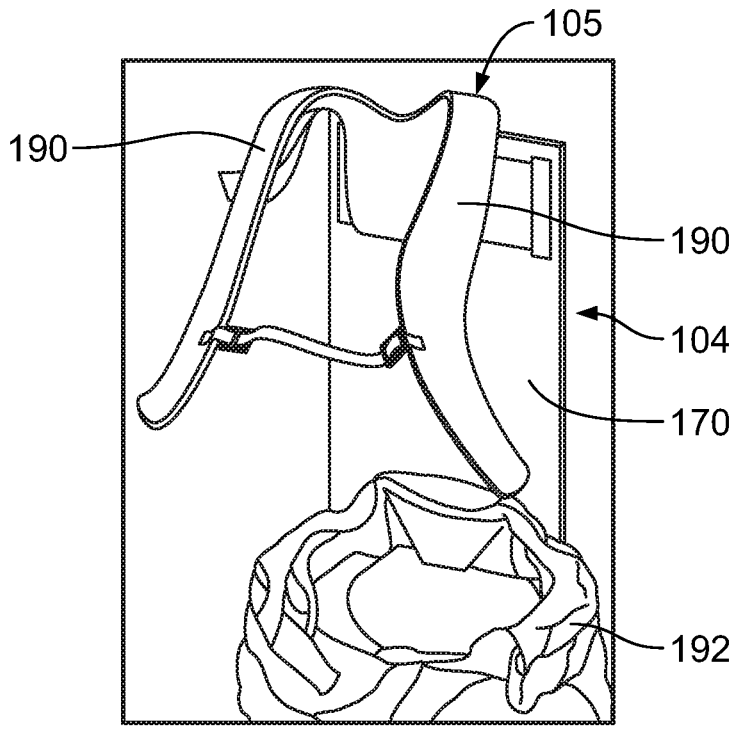
FIG. 17 illustrates a perspective front view of a harness coupled to a backpack assembly, according to an embodiment of the present disclosure.

FIG. 17 illustrates a perspective front view of the harness 105 coupled to the backpack assembly 104, according to an embodiment of the present disclosure. The harness 105 may include shoulder straps 190 and/or a waist or hip belt or strap 192, which allow the individual to comfortably wear the backpack assembly 104.

Referring to FIGS. 1-17, in operation, the individual may walk through an area wearing the backpack assembly 104. When a structure to be sanitized is found, the individual may position grasp the handle 108 and position the sanitizing head 106 as desired, such as by extending and/or rotating the sanitizing head 106 relative to the handle 108. The individual may then engage an activation button on the handle 108, for example, to activate the UV lamp 140 to emit sanitizing UV light onto the structure. As the UV lamp 140 is activated, air 150 is drawn into the shroud 112 to cool the UV lamp 140, and divert any generated ozone into the backpack assembly 104, where it is filtered by the air filters 183.

The extendable wand assembly 102 allows the sanitizing head 106 to reach distant areas, such as over an entire set of three passenger seats, from a row within an internal cabin of a commercial aircraft.

Figure 18:
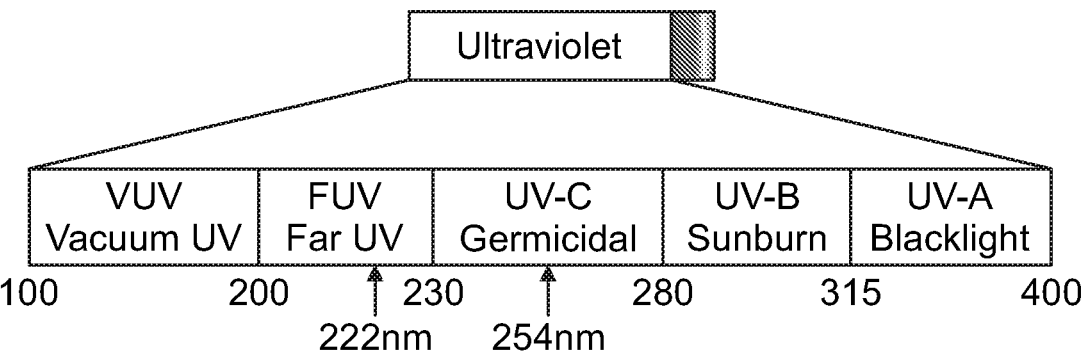
FIG. 18 illustrates an ultraviolet light spectrum.

FIG. 18 illustrates an ultraviolet light spectrum. Referring to FIGS. 1-18, in at least one embodiment, the sanitizing head 106 is configured to emit sanitizing UV light (through operation of the UV lamp 140) within a far UV spectrum, such as between 200 nm to 230 nm. In at least one embodiment, the sanitizing head 106 emits sanitizing UV light having a wavelength of 222 nm.

Figure 19:
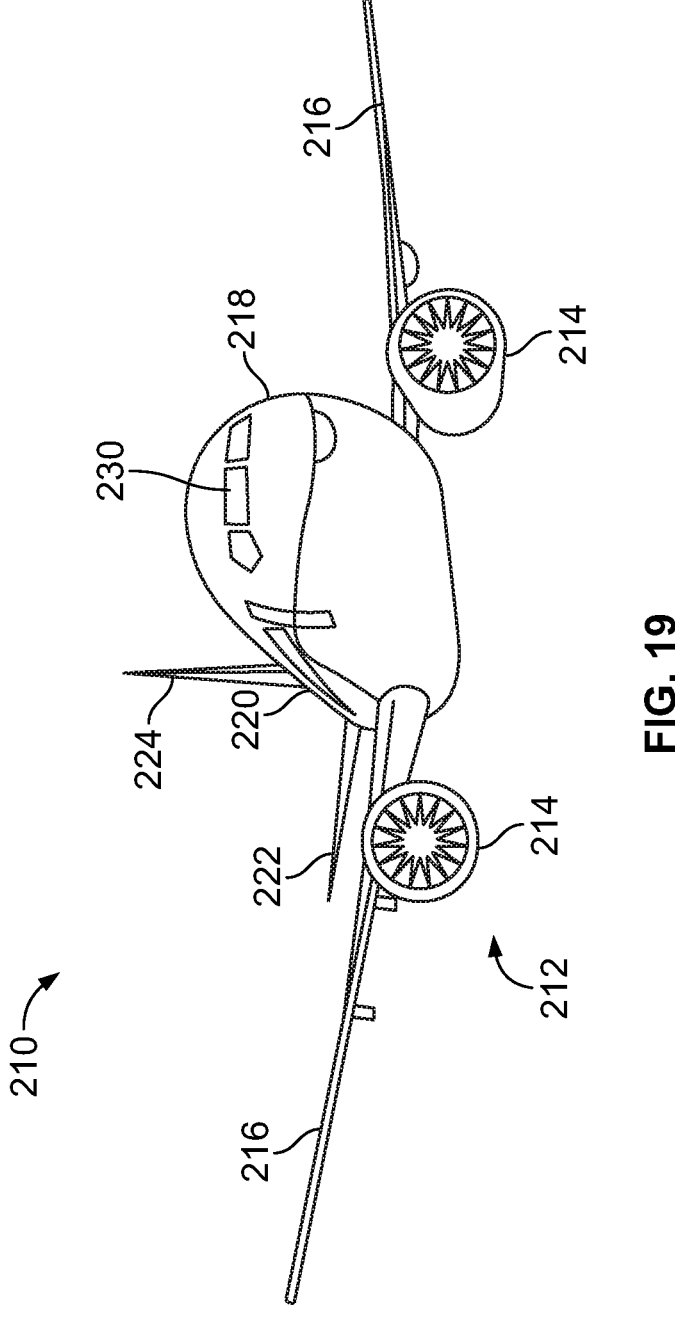
FIG. 19 illustrates a perspective front view of an aircraft, according to an embodiment of the present disclosure.

FIG. 19 illustrates a perspective front view of an aircraft 210, according to an embodiment of the present disclosure. The aircraft 210 includes a propulsion system 212 that includes engines 214, for example. Optionally, the propulsion system 212 may include more engines 14 than shown. The engines 214 are carried by wings 216 of the aircraft 210. In other embodiments, the engines 214 may be carried by a fuselage 218 and/or an empennage 220. The empennage 220 may also support horizontal stabilizers 222 and a vertical stabilizer 224.

The fuselage 218 of the aircraft 210 defines an internal cabin 230, which includes a flight deck or cockpit, one or more work sections (for example, galleys, personnel carry-on baggage areas, and the like), one or more passenger sections (for example, first class, business class, and coach sections), one or more lavatories, and/or the like. The internal cabin 230 includes one or more lavatory systems, lavatory units, or lavatories, as described herein.

Alternatively, instead of an aircraft, embodiments of the present disclosure may be used with various other vehicles, such as automobiles, buses, locomotives and train cars, watercraft, and the like. Further, embodiments of the present disclosure may be used with respect to fixed structures, such as commercial and residential buildings.

Figures 20A, 20B:
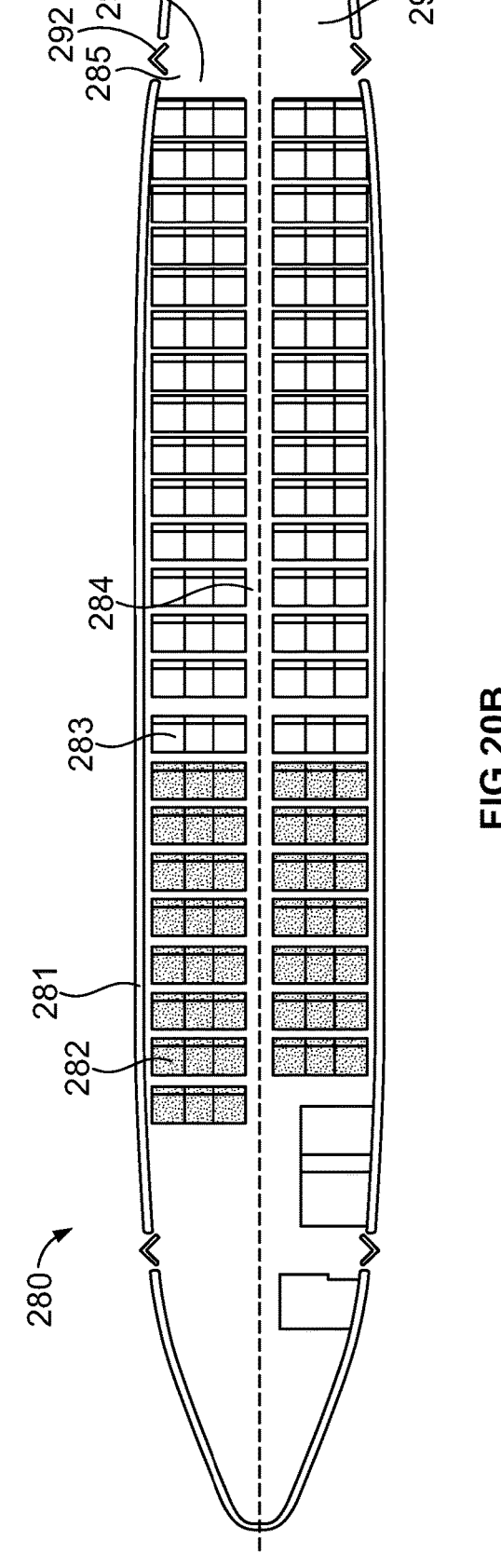
FIG. 20A illustrates a top plan view of an internal cabin of an aircraft, according to an embodiment of the present disclosure.
FIG. 20B illustrates a top plan view of an internal cabin of an aircraft, according to an embodiment of the present disclosure.

FIG. 20A illustrates a top plan view of an internal cabin 230 of an aircraft, according to an embodiment of the present disclosure. The internal cabin 230 may be within the fuselage 232 of the aircraft, such as the fuselage 218 of FIG. 19. For example, one or more fuselage walls may define the internal cabin 230. The internal cabin 230 includes multiple sections, including a front section 233, a first class section 234, a business class section 236, a front galley station 238, an expanded economy or coach section 240, a standard economy of coach section 242, and an aft section 244, which may include multiple lavatories and galley stations. It is to be understood that the internal cabin 230 may include more or less sections than shown. For example, the internal cabin 230 may not include a first class section, and may include more or less galley stations than shown. Each of the sections may be separated by a cabin transition area 246, which may include class divider assemblies between aisles 248.

As shown in FIG. 20A, the internal cabin 230 includes two aisles 250 and 252 that lead to the aft section 244. Optionally, the internal cabin 230 may have less or more aisles than shown. For example, the internal cabin 230 may include a single aisle that extends through the center of the internal cabin 230 that leads to the aft section 244.

The aisles 248, 250, and 252 extend to egress paths or door passageways 260. Exit doors 262 are located at ends of the egress paths 260. The egress paths 260 may be perpendicular to the aisles 248, 250, and 252. The internal cabin 230 may include more egress paths 260 at different locations than shown. The portable sanitizing system 100 shown and described with respect to FIGS. 1-18 may be used to sanitize various structures within the internal cabin 230, such as passenger seats, monuments, stowage bin assemblies, components on and within lavatories, galley equipment and components, and/or the like.

FIG. 20B illustrates a top plan view of an internal cabin 280 of an aircraft, according to an embodiment of the present disclosure. The internal cabin 280 is an example of the internal cabin 230 shown in FIG. 19. The internal cabin 280 may be within a fuselage 281 of the aircraft. For example, one or more fuselage walls may define the internal cabin 280. The internal cabin 280 includes multiple sections, including a main cabin 282 having passenger seats 283, and an aft section 285 behind the main cabin 282. It is to be understood that the internal cabin 280 may include more or less sections than shown.

The internal cabin 280 may include a single aisle 284 that leads to the aft section 285. The single aisle 284 may extend through the center of the internal cabin 280 that leads to the aft section 285. For example, the single aisle 284 may be coaxially aligned with a central longitudinal plane of the internal cabin 280.

The aisle 284 extends to an egress path or door passageway 290. Exit doors 292 are located at ends of the egress path 290. The egress path 290 may be perpendicular to the aisle 284. The internal cabin 280 may include more egress paths than shown. The portable sanitizing system 100 shown and described with respect to FIGS. 1-18 may be used to sanitize various structures within the internal cabin 230, such as passenger seats, monuments, stowage bin assemblies, components on and within lavatories, galley equipment and components, and/or the like.

Figure 21:
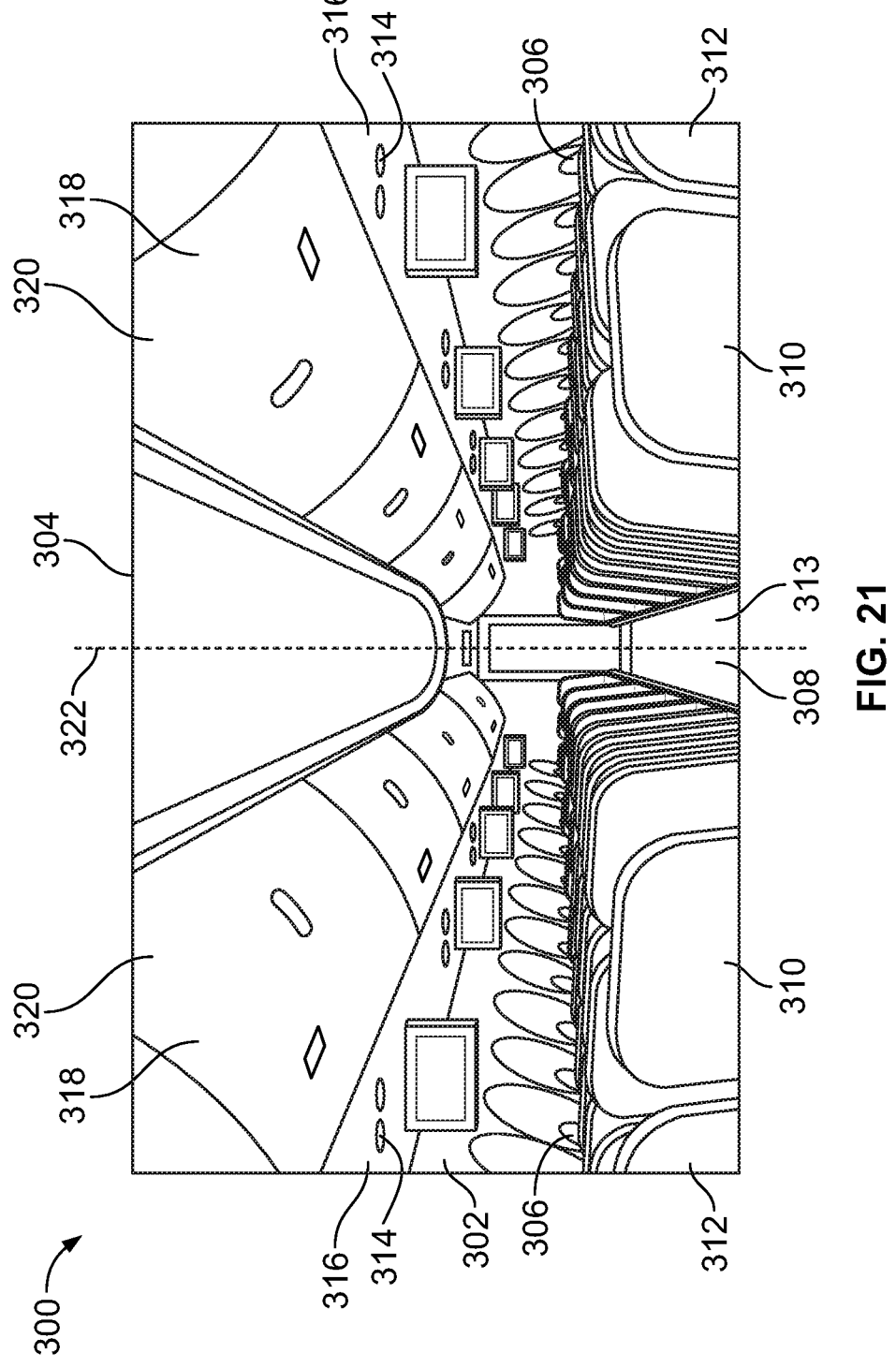
FIG. 21 illustrates a perspective interior view of an internal cabin of an aircraft, according to an embodiment of the present disclosure.

FIG. 21 illustrates a perspective interior view of an internal cabin 300 of an aircraft, according to an embodiment of the present disclosure. The internal cabin 300 includes outboard walls 302 connected to a ceiling 304. Windows 306 may be formed within the outboard walls 302. A floor 308 supports rows of seats 310. As shown in FIG. 21, a row 312 may include two seats 310 on either side of an aisle 313. However, the row 312 may include more or less seats 310 than shown. Additionally, the internal cabin 300 may include more aisles than shown.

Passenger service units (PSUs) 314 are secured between an outboard wall 302 and the ceiling 304 on either side of the aisle 313. The PSUs 314 extend between a front end and rear end of the internal cabin 300. For example, a PSU 314 may be positioned over each seat 310 within a row 312. Each PSU 314 may include a housing 316 that generally contains vents, reading lights, an oxygen bag drop panel, an attendant request button, and other such controls over each seat 310 (or groups of seats) within a row 312.

Overhead stowage bin assemblies 318 are secured to the ceiling 304 and/or the outboard wall 302 above and inboard from the PSU 314 on either side of the aisle 313. The overhead stowage bin assemblies 318 are secured over the seats 310. The overhead stowage bin assemblies 318 extend between the front and rear end of the internal cabin 300. Each stowage bin assembly 318 may include a pivot bin or bucket 320 pivotally secured to a strongback (hidden from view in FIG. 21). The overhead stowage bin assemblies 318 may be positioned above and inboard from lower surfaces of the PSUs 314. The overhead stowage bin assemblies 318 are configured to be pivoted open in order to receive passenger carry-on baggage and personal items, for example.

As used herein, the term "outboard" means a position that is further away from a central longitudinal plane 322 of the internal cabin 300 as compared to another component. The term "inboard" means a position that is closer to the central longitudinal plane 322 of the internal cabin 300 as compared to another component. For example, a lower surface of a PSU 314 may be outboard in relation to a stowage bin assembly 318.

The portable sanitizing system 100 shown and described with respect to FIGS. 1-18 may be used to sanitize various structures shown within the internal cabin 300.

When not in use, the portable sanitizing system 100 may be stored within a closet, galley cart bay, or galley cart, such as within the internal cabin of the vehicle.

Figure 22:
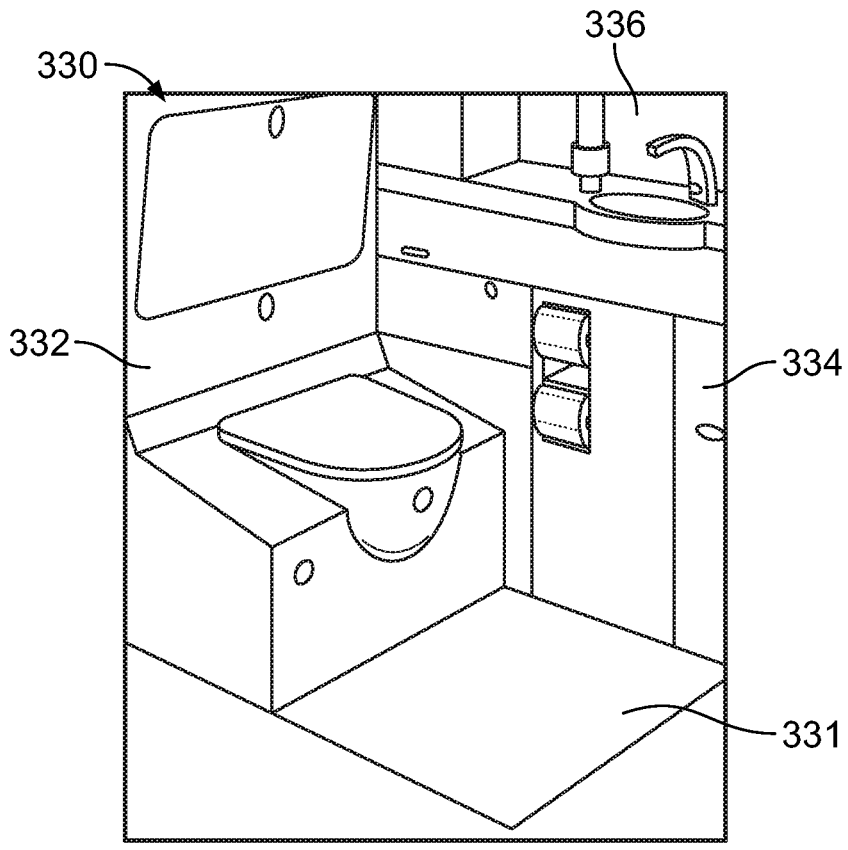
FIG. 22 illustrates a perspective internal view of a lavatory within an internal cabin of an aircraft.

FIG. 22 illustrates a perspective internal view of a lavatory 330 within an internal cabin of a vehicle, such as any of the internal cabins described herein. The lavatory 330 is an example of an enclosed space, monument or chamber, such as within the internal cabin a vehicle. The lavatory 330 may be onboard an aircraft, as described above. Optionally, the lavatory 330 may be onboard various other vehicles. In other embodiments, the lavatory 330 may be within a fixed structure, such as a commercial or residential building. The lavatory 330 includes a base floor 331 that supports a toilet 332, cabinets 334, and a sink 336 or wash basin. The lavatory 330 may be arranged differently than shown. The lavatory 330 may include more or less components than shown. The portable sanitizing system 100 shown and described with respect to FIGS. 1-18 may be used to sanitize the various structures, components, and surfaces within the lavatory 330.

Figure 23:
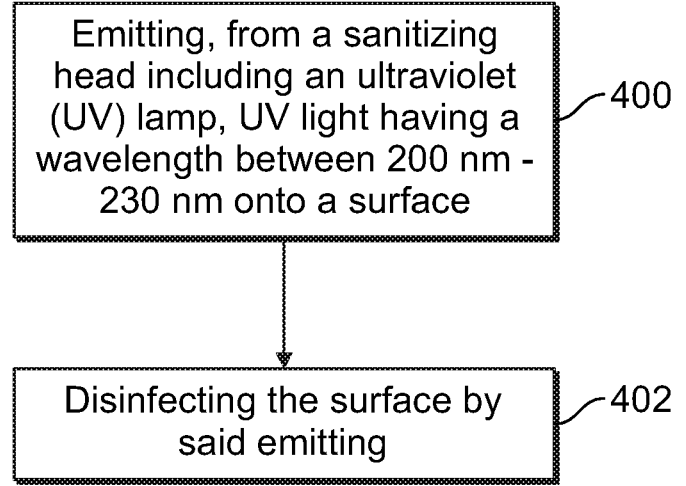
FIG. 23 illustrates a flow chart of a portable sanitizing method, according to an embodiment of the present disclosure.

FIG. 23 illustrates a flow chart of a portable sanitizing method, according to an embodiment of the present disclosure. The method includes emitting (400), from a sanitizing head including an ultraviolet (UV) lamp, UV light having a wavelength between 200 nm-230 nm onto a surface; and disinfecting (402) the surface by said emitting (400). In at least one embodiment, said emitting (400) includes emitting the UV light having a wavelength of 222 nm.

In at least embodiment, the portable sanitizing method further includes moveably coupling a handle to the sanitizing head. For example, said moveably coupling includes one or both of linearly translating or swiveling the sanitizing head in relation to the handle.

In at least one embodiment, the portable sanitizing method includes coupling a backpack assembly to the sanitizing head through a hose.

Referring to FIGS. 1-23, the portable sanitizing system 100 can be used to safely and effectively sanitize high-touch surfaces in the flight deck and internal cabin in a timely and cost-effective manner. UV disinfection allows the internal cabin to be quickly and effectively disinfected, such as between flights. In at least one embodiment, the portable sanitizing system 100 is used to augment a cleaning process, such as after manual cleaning.

Figure 24:
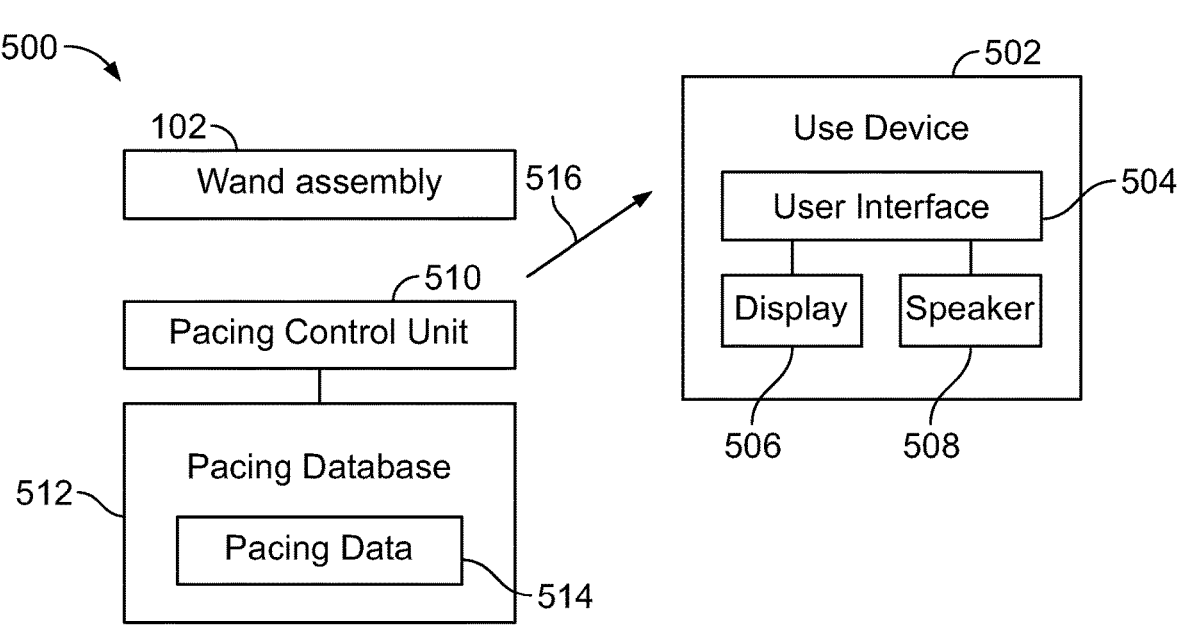
FIG. 24 illustrates a schematic block diagram of a UV light pacing system, according to an embodiment of the present disclosure.

FIG. 24 illustrates a schematic block diagram of a UV light pacing system 500, according to an embodiment of the present disclosure. The UV light pacing system 500 includes the wand assembly 102, such as part of the UV sanitizing system 100 (shown in FIG. 1). The wand assembly 102 includes a sanitizing head, as described herein. The sanitizing head includes a UV lamp that is configured to emit sanitizing UV light, such as having a wavelength between 220-230 nm. The wand assembly 102 may include a handle that allows the sanitizing head to move relative to the handle. Optionally, the wand assembly 102 may include a sanitizing head and handle that are fixed in relation to one another.

The UV light pacing system 500 also includes a user device 502. In at least one embodiment, the user device 502 is a handheld device, such as a smart phone or smart tablet. As another example, the user device 502 may be a computer, such as a desktop or laptop computer.

The user device 502 includes a user interface 504, a display 506, and a speaker 508, such as a speaker formed on or in, or otherwise coupled to the user device 502, or a headphone(s) coupled to the user device 502 via a wired or wireless connection. The user interface 504 includes an input device, such as a keyboard, mouse, or the like. The display 506 includes a monitor or screen. In at least one embodiment, the user interface 504 and the display 506 are integrated as a touchscreen interface.

A pacing control unit 510 is in communication with the user device 502, such as through one or more wired or wireless connections. For example, the pacing control unit 510 may be in communication with the user device 502 through Bluetooth, WiFi, and/or Internet connectivity. The pacing control unit 510 may be remotely located from the user device 502. In at least one other embodiment, the user device 502 may include the pacing control unit 510. For example, the pacing control unit 510 may be contained within a housing of the user device 502.

The pacing control unit 510 is also in communication with a pacing database 512, which stores pacing data 514, such as through one or more wired or wireless connections. For example, the pacing control unit 510 may be in communication with the pacing database 512 through Bluetooth, WiFi, and/or Internet connectivity. The pacing control unit

510 may be remotely located from the pacing database 512. In at least one other embodiment, the pacing control unit 510 may be co-located with the pacing database 512. For example, the pacing control unit 510 and the pacing database 512 may be contained within a common computer workstation. As another example, the pacing control unit 510 and the pacing database 512 may be contained within the user device 502.

The pacing database 512 stores pacing data 514 regarding one or more items to be disinfected. Pacing information regarding a selected item for disinfection is determined from the pacing data 514. For example, the pacing data 514 includes pacing information regarding numerous items to be disinfected. An item to be disinfected is selected through the user device 502, and the pacing control unit 510 analyzes the pacing data 514 to determine the pacing information for the item, as stored within the pacing data 514.

The pacing data 514 may include information regarding ultraviolet (UV) disinfecting information for various items (such as surfaces, components, and the like) and/or pathogens. For example, the pacing data 514 includes UV disinfecting dosage for a particular item in relation to a particular pathogen to neutralize.

In operation, a user communicates with the pacing control unit 510 through the user device 502. The user may select an item to be disinfected. The pacing control unit 510 analyzes the item for disinfection by reviewing the pacing data 514 stored in the pacing database 512. The pacing control unit 510 then outputs a pacing signal 516 that includes pacing information for disinfecting the item to the user device 502. At least a portion of the pacing information may be shown on the display. The pacing information may include a distance to a surface of the item, time for disinfecting, and a rate at which the wand assembly 102 should be swept over or otherwise moved in relation to the item. The pacing information may also include a pacing audio signal that is broadcast through the speaker 508. The pacing audio signal, as broadcast by the speaker 508, is an audio cue that allows the user to synchronize the pace of sweeping or otherwise moving the wand assembly 102. In this manner, the pacing control unit 510 allows the user to effectively and efficiently disinfect the item.

As described herein, the UV light pacing system 500 includes the wand assembly 102 including a UV lamp that is configured to emit UV light. The user device 502 is configured to allow a user to select an item to be disinfected with the UV light. The pacing control unit 510 is in communication with the user device 502. The pacing control unit 510 is configured to output the pacing signal 516 to the user device 502. The pacing signal 516 includes pacing information regarding operation of the wand assembly 102 to disinfect the item. For example, the pacing information includes instructions (which are shown on the display 506) for operating the wand assembly 102 to disinfect the item. As another example, the pacing information includes one or more audio cues (which are broadcast by the speaker 508) for pacing motion of the wand assembly 102 during a disinfection process of the item. In at least one embodiment, the pacing information includes both the instructions, as shown on the display 506, and the audio cues, as broadcast by the speaker 508.

In at least one embodiment, the pacing data 514, which includes the pacing information, is saved in the pacing database 512. The pacing control unit 510 is configured to analyze the stored pacing data 514. Further, the pacing data 514 can be shared with others at any time. For example, the pacing data 514 can be saved with respect to a complete maintenance record and history of UV exposure. The pacing data 514 can be reviewed to determine which areas to prioritize for disinfecting. In at least one embodiment, the pacing data 514 can be saved along with sensor data for robot or human performance feedback contemporaneously or later. The sensor data can be basic, simple data to reduce data storage requirements, or as complex, such as video data showing a cleaning process. In this manner, the pacing data 514 may provide feedback information regarding surfaces that have been cleaned, the effectiveness of such cleaning, and surfaces that need to be cleaned.

As used herein, the term "control unit," "central processing unit," "CPU," "computer," or the like may include any processor-based or microprocessor-based system including systems using microcontrollers, reduced instruction set computers (RISC), application specific integrated circuits (ASICs), logic circuits, and any other circuit or processor including hardware, software, or a combination thereof capable of executing the functions described herein. Such are exemplary only, and are thus not intended to limit in any way the definition and/or meaning of such terms. For example, the pacing control unit 510 may be or include one or more processors that are configured to control operation, as described herein.

The pacing control unit 510 is configured to execute a set of instructions that are stored in one or more data storage units or elements (such as one or more memories), in order to process data. For example, the pacing control unit 510 may include or be coupled to one or more memories. The data storage units may also store data or other information as desired or needed. The data storage units may be in the form of an information source or a physical memory element within a processing machine.

The set of instructions may include various commands that instruct the pacing control unit 510 as a processing machine to perform specific operations such as the methods and processes of the various embodiments of the subject matter described herein. The set of instructions may be in the form of a software program. The software may be in various forms such as system software or application software. Further, the software may be in the form of a collection of separate programs, a program subset within a larger program, or a portion of a program. The software may also include modular programming in the form of object-oriented programming. The processing of input data by the processing machine may be in response to user commands, or in response to results of previous processing, or in response to a request made by another processing machine.

The diagrams of embodiments herein may illustrate one or more control or processing units, such as the pacing control unit 510. It is to be understood that the processing or control units may represent circuits, circuitry, or portions thereof that may be implemented as hardware with associated instructions (e.g., software stored on a tangible and non-transitory computer readable storage medium, such as a computer hard drive, ROM, RAM, or the like) that perform the operations described herein. The hardware may include state machine circuitry hardwired to perform the functions described herein. Optionally, the hardware may include electronic circuits that include and/or are connected to one or more logic-based devices, such as microprocessors, processors, controllers, or the like. Optionally, the pacing control unit 510 may represent processing circuitry such as one or more of a field programmable gate array (FPGA), application specific integrated circuit (ASIC), microprocessor(s), and/or the like. The circuits in various embodiments may be configured to execute one or more algorithms to perform functions described herein. The one or more algorithms may include aspects of embodiments disclosed herein, whether or not expressly identified in a flowchart or a method.

As used herein, the terms "software" and "firmware" are interchangeable, and include any computer program stored in a data storage unit (for example, one or more memories) for execution by a computer, including RAM memory, ROM memory, EPROM memory, EEPROM memory, and non-volatile RAM (NVRAM) memory. The above data storage unit types are exemplary only, and are thus not limiting as to the types of memory usable for storage of a computer program.

Figure 25:
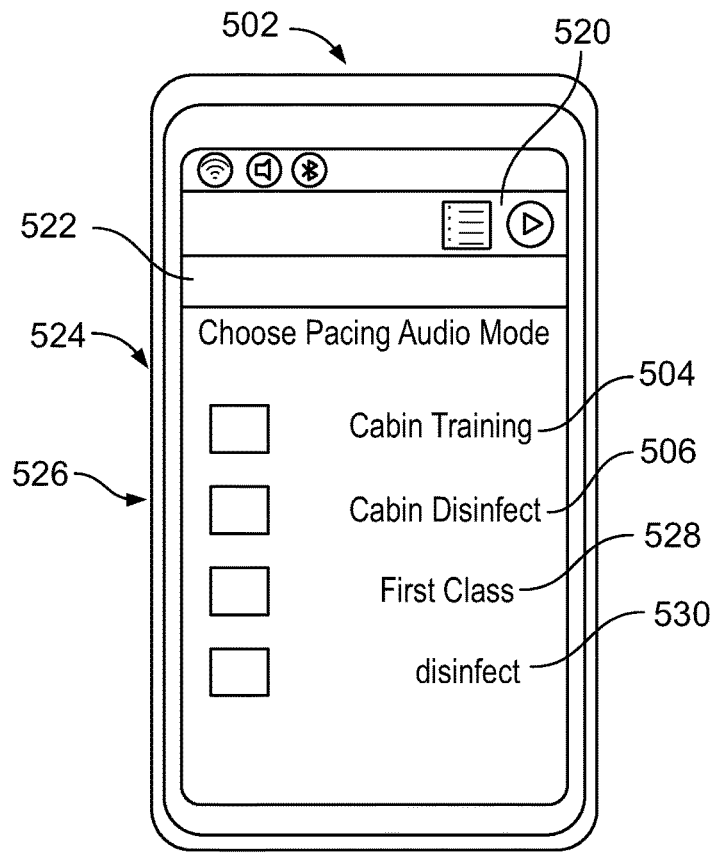
FIG. 25 illustrates a front view of a user device, according to an embodiment of the present disclosure.

FIG. 25 illustrates a front view of the user device 502, according to an embodiment of the present disclosure. As shown, the user device 502 is a handheld smart device (such as a smart phone or smart tablet) that includes a touchscreen interface 520 that integrates the user interface 504 and the display 508.

Referring to FIGS. 24-25, the pacing control unit 510 shows a pacing menu screen 522 on the user device 502. The pacing menu screen 522 allows a user to select a particular pacing mode. For example, the pacing menu screen 522 shows a first training option 524, such as for a cabin of a particular type of aircraft, and a disinfecting pacing option 526 for the cabin. The pacing menu screen 522 may also show a second training option 528, such as for a different area within the aircraft, and a disinfecting pacing option 530 for the different area.

The pacing control unit 510 provides the training options and disinfecting pacing options to provide the user audio cures to provide a correct of amount of time for exposure of areas within the aircraft to disinfecting UV light, as emitted by the wand assembly 102. As such, the user may pace movement of the wand assembly 102 during sanitation, such as via the audio signals broadcast by the pacing control unit 510 through the speaker 508, to ensure a correct disinfecting dose of UV light in mJ/cm$^2$.

The pacing information, as included in the pacing signal 516 output by the pacing control unit 510 to the user device (and as show on the display 506 and/or broadcast through the speaker 508) includes a range of the wand assembly 102 to a surface to be disinfected, a time of UV illumination of the surface, and a rate of sweep of the wand assembly 102 (such as a rate for sweeping the wand assembly 102 back and forth over the surface). In at least one embodiment, the rate of sweep is guided by an audio signal broadcast through the speaker 508.

The training options may include audio files for a pace of sweeping or otherwise moving the wand assembly 102 and detailed instructions to ensure effective and efficient sanitation of items. A user can listen to such audio files to learn the proper sweep rate of the wand assembly 102 for a particular item or items. The disinfecting pacing options may include audio files for a pace of sweeping or otherwise moving the wand assembly 102 without detailed instructions.

Figure 26:
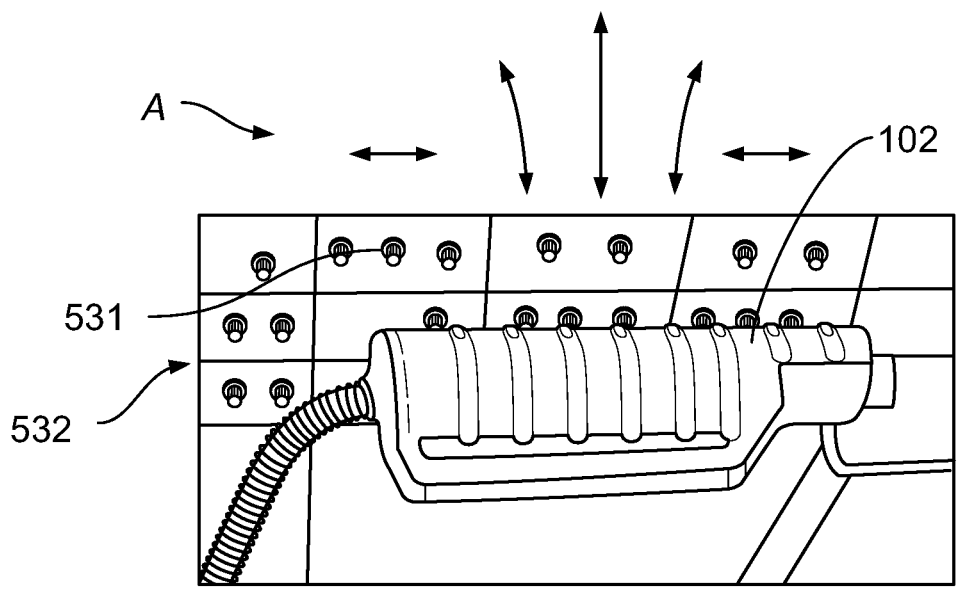
FIG. 26 illustrates a perspective view of a wand assembly in relation to controls within a flight deck, according to an embodiment of the present disclosure.

FIG. 26 illustrates a perspective view of the wand assembly 102 in relation to controls 531 within a flight deck 532, according to an embodiment of the present disclosure. The controls 531 are one example of items to be disinfected by UV light. Other examples include seats, stowage bin assemblies, walls, ceilings, galley carts, counters, cabinets, toilets, sinks, floors, and/or the like. The wand assembly 102 is spaced apart from the controls 531 a particular range, as noted in the pacing information, and swept in various directions in relation to the controls 531, such as in the directions of arrows A.

Referring to FIGS. 24-26, a user selects the item(s) that is to be disinfected via the user device 502. The pacing control unit 510 retrieves the pacing data 514 regarding the selected item(s) from the pacing database 512. The pacing control unit 510 then outputs the pacing signal 516 that includes the pacing information for the item(s) (such as the controls 531) to the user device 502. The pacing information, as shown on the display 506 and/or broadcast through the speaker 508, assists the user with sweeping the wand assembly 102 in relation to the item(s) to effectively and efficiently sanitize and disinfect the item(s).

FIG. 27 illustrates a spreadsheet 540 of pacing information 542, according to an embodiment of the present disclosure. The pacing signal 516 as output by the pacing control unit 510 to the user device 502 (as shown in FIG. 24) includes the pacing information 542. The pacing information 542 shown in FIG. 27 is merely exemplary.

The pacing information 542 includes wand movement speed 546. Referring to FIGS. 24 and 27, the pacing control unit 510 can broadcast an audio signal (such as a repeating beat) that is set to the proper pace for disinfecting, as shown in the wand movement speed 546. The audio signal, as broadcast through the speaker 508, allows the user to move the wand assembly 102 at the proper pace to ensure effective disinfecting of the item.

Referring to FIGS. 24-27, the user device 502 may include an application ("app") stored in memory regarding disinfecting surfaces. The app may be shown on the display 506. The pacing control unit 510 may operate the app, as described herein. The app may broadcast audio files for selected items to be disinfected.

As an example, the pacing control unit 520 may output the pacing signal 516, which, for example, includes instructions and pacing for a center flight control console on a flight deck. The pacing signal 516 is received by the user device 502. The pacing signal 516 includes an audio file that provides guidance to the user for sweeping or otherwise moving the wand assembly 102. The total sweep time is intended to give a specific dose over the entire center console to effectively and efficiently disinfect the center console. For example, the instructions may indicate (either via text or audio signals) "begin at the aft most part of the center console and sweep forward at an even pace, taking 10 seconds to reach the forward end of the console." Next, the instructions may countdown by indicating, via an audio broadcast, "Begin: 10, 9, 8, 7, 6, 5, 4, 3, 2, 1. End of console." Next, the instructions may indicate, "Move wand to right seat arm rest . . . ." A metronome type beat can be played at each second with a cymbal crash sound effect or other appropriate sound at the end of the sweep period.

Referring still to FIGS. 24-27, certain embodiments of the present disclosure provide a method of pacing UV disinfection of a predetermined surface. The method includes calculating a wand speed. The wand speed is calculated by the user selecting an item to be disinfected through the user device, and the pacing control unit 510 retrieving the pacing data 514 associated with the item from the pacing database 512. The pacing data 514 includes the wand speed. The pacing data 514, as output by the pacing control unit 512, provides audio cues (as broadcast through the speaker 508) regarding a rate at which to move the wand, assembly 102 and may provide feedback (such as audio instructions for a sweep time) so the user can maintain said rate.

In at least one embodiment, the audio cues may be or otherwise include a series of audio files to provide voice instruction and pacing for the area to be cleaned, or may include a tone such as a metronome beat and and/or cymbal sounds to indicate the end of the sweep period. The audio files may be loaded into a computer program, such as a mobile app, to act as an audio coach to instruct the user how long to hold the UV wand over the area to disinfect. The computer program may include a mobile app or other computer program to manage the audio files.

In at least one embodiment, the wand speed is calculated by entering known parameters such as range to surface, irradiance of wand, disinfection energy required to sanitize the surface, wand length, and wand width to conduct calculations for time required to disinfect surfaces.

Figure 28:
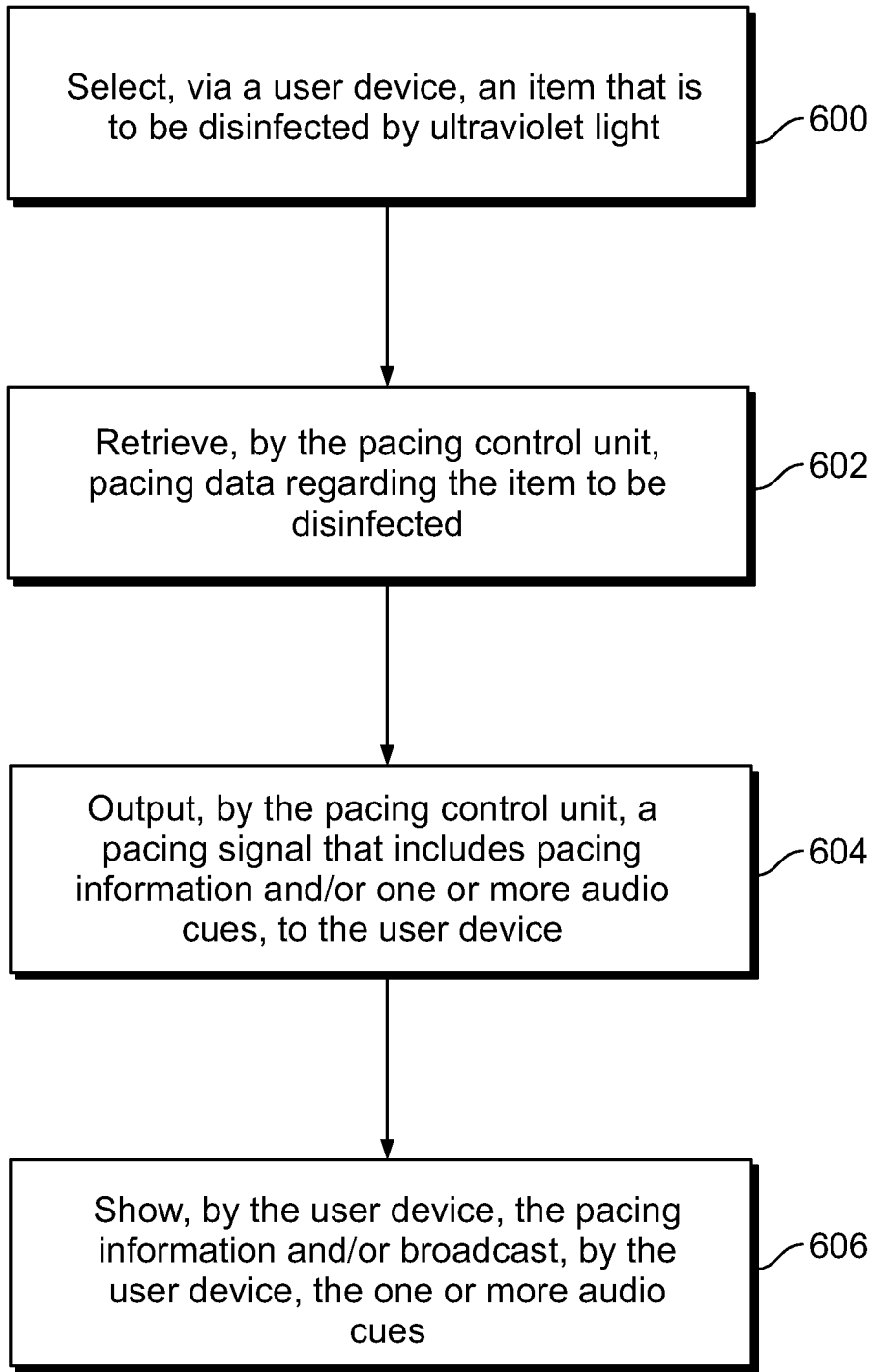
FIG. 28 illustrates a flow chart of a UV pacing method, according to an embodiment of the present disclosure.

FIG. 28 illustrates a flow chart of a UV pacing method, according to an embodiment of the present disclosure. Referring to FIGS. 24 and 28, at 600, an individual selects, on the user device 504, an item to be disinfected by UV light. At 602, the pacing control unit 510 retrieves the pacing data 514 regarding the item to be disinfected from the pacing database 512. At 604, the pacing control unit 510 outputs the pacing signal 516, which includes the pacing information for the item to be disinfected as well as one or more audio cues, to the user device 502. At 606, the user device 502 shows the pacing information and/or broadcasts the one or more audio cues that assist the user in moving the wand assembly 102 to effectively and efficiently disinfect the item.

As described herein, embodiments of the present disclosure provide systems and a methods for efficiently sterilizing surfaces, components, structures, and/or the like within an internal cabin of a vehicle. Further, embodiments of the present disclosure provide compact, easy-to-use, and safe systems and methods for using UV light to sterilize surfaces within an internal cabin.

Further, the disclosure comprises embodiments according to the following clauses:

Clause 1. An ultraviolet (UV) light pacing system, comprising:

a wand assembly including a UV lamp that is configured to emit UV light;

a user device configured to allow a user to select an item to be disinfected with the UV light; and a pacing control unit in communication with the user device, wherein the pacing control unit is configured to output a pacing signal to the user device, wherein the pacing signal includes pacing information regarding operation of the wand assembly to disinfect the item.

Clause 2. The UV light pacing system of Clause 1, wherein the pacing information includes instructions for operating the wand assembly to disinfect the item, and wherein the instructions are shown on a display of the user device.

Clause 3. The UV light pacing system of Clauses 1 or 2, wherein the pacing information includes one or more audio cues for pacing motion of the wand assembly during a disinfection process of the item, and wherein the one or more audio cues are broadcast by a speaker of the user device.

Clause 4. The UV light pacing system of any of Clauses 1-3, wherein the user device is a handheld device.

Clause 5. The UV light pacing system of any of Clauses 1-4, wherein the user device includes the pacing control unit.

Clause 6. The UV light pacing system of any of Clauses 1-5, further comprising a pacing database that stores pacing data regarding the item, wherein the pacing control unit is in communication with the pacing database, and wherein the pacing control unit is configured to determine the pacing information from the pacing data.

Clause 7. The UV light pacing system of any of Clauses 1-6, wherein the user device includes the pacing database.

Clause 8. The UV light pacing system of any of Clauses 1-7, wherein the user device comprises a display, and wherein the pacing control unit is configured to show a pacing menu screen on the display.

Clause 9. The UV light pacing system of Clause 8, wherein the pacing menu screen comprises one or more training options.

Clause 10. The UV light pacing system of any of Clauses 1-9, wherein the pacing information includes wand movement speed.

Clause 11. The UV light pacing system of any of Clauses 1-10, wherein the item comprises a passenger seat, a monument, a stowage bin assembly, a component within a lavatory, a component within a galley, or a component within a flight deck.

Clause 12. The UV light pacing system of any of Clauses 1-11, wherein the UV lamp is configured to emit the UV light having a wavelength between 200 nm-230 nm.

Clause 13. The UV light pacing system of any of Clauses 1-11, wherein the UV lamp is configured to emit the UV light having a wavelength of 222 nm.

Clause 14. The UV light pacing system of any of clauses 1-11, wherein the UV lamp is configured to emit the UV light having a wavelength of 230 nm-280 nm.

Clause 15. The UV light pacing system of any of Clauses 1-11, wherein the UV lamp is configured to emit the UV light having a wavelength of 254 nm.

Clause 16. An ultraviolet (UV) light pacing method, comprising:

using a wand assembly including a UV lamp to emit UV light;

selecting, by a user device. an item to be disinfected with the UV light; and outputting, from a pacing control unit in communication with the user device, a pacing signal to the user device, wherein the pacing signal includes pacing information regarding operation of the wand assembly to disinfect the item.

Clause 17. The UV light pacing method of Clause 16, wherein the pacing information includes instructions for operating the wand assembly to disinfect the item, and wherein the method further comprises showing the instructions on a display of the user device.

Clause 18. The UV light pacing method of Clause 16 or 17, wherein the pacing information includes one or more audio cues for pacing motion of the wand assembly during a disinfection process of the item, and wherein the method further comprises broadcasting the one or more audio cues by a speaker of the user device.

Clause 19. The UV light pacing method of any of Clauses 16-18, further comprising:

storing, in a pacing database, pacing data regarding the item;

communicatively coupling the pacing control unit with the pacing database; and determining, by the pacing control unit, the pacing information from the pacing data.

Clause 20. The UV light pacing method of any of Clauses 16-19, further comprising showing, by the pacing control unit, a pacing menu screen on the display.

Clause 21. The UV light pacing method of Clause 20, wherein said showing comprises showing one or more training options.

Clause 22. The UV light pacing method of any of Clauses 16-21, wherein said using comprises operating the UV lamp to emit the UV light having a wavelength between 200 nm-230 nm.

Clause 23. The UV light pacing method of any of Clauses 16-21, wherein said using comprises operating the UV lamp to emit the UV light having a wavelength of 222 nm.

Clause 24. The UV light pacing method of any of Clauses 16-21, wherein said using comprises operating the UV lamp to emit the UV light having a wavelength between 230 nm-280 nm.

Clause 25. The UV light pacing method of any of Clauses 16-21, wherein said using comprises operating the UV lamp to emit the UV light having a wavelength of 254 nm.

Clause 26. An ultraviolet (UV) light pacing system, comprising:

a wand assembly including a UV lamp that is configured to emit UV light;

a user device configured to allow a user to select an item to be disinfected with the UV light, wherein the user device comprises a display and a speaker;

a pacing database that stores pacing data regarding the item; and a pacing control unit in communication with the user device and the pacing database, wherein the pacing control unit is configured to determine the pacing information from the pacing data, wherein the pacing control unit is configured to output a pacing signal to the user device, wherein the pacing signal includes pacing information regarding operation of the wand assembly to disinfect the item, and wherein the pacing information includes:

instructions for operating the wand assembly to disinfect the item, and wherein the instructions are shown on the display of the user device; and one or more audio cues for pacing motion of the wand assembly during a disinfection process of the item, and wherein the one or more audio cues are broadcast by the speaker of the user device.

While various spatial and directional terms, such as top, bottom, lower, mid, lateral, horizontal, vertical, front and the like can be used to describe embodiments of the present disclosure, it is understood that such terms are merely used with respect to the orientations shown in the drawings. The orientations can be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described embodiments (and/or aspects thereof) can be used in combination with each other. In addition, many modifications can be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims and the detailed description herein, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and can include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. An ultraviolet (UV) light pacing system, comprising:

a backpack assembly;

a wand assembly removably coupled to the backpack assembly, the wand assembly including:

a sanitizing head containing a UV lamp that is configured to emit UV light; and an elongate handle connected to the sanitizing head via a coupler, wherein the coupler allows selective pivoting of the elongate handle relative to the sanitizing head into a first position in which the elongate handle is pivoted toward the sanitizing head for coupling the wand assembly onto the backpack assembly, and into a second position in which the elongate handle is pivoted away from the sanitizing head for extending the length of the wand assembly when the wand assembly is removed from the backpack assembly for sanitizing purposes;

a user device configured to allow a user to select an item to be disinfected with the UV light;

a pacing control unit in communication with the user device, wherein the pacing control unit is configured to output a pacing signal to the user device, wherein the pacing signal includes pacing information regarding operation of the wand assembly to disinfect the item to be disinfected; and a pacing database configured to store pacing data regarding the item to be disinfected, wherein the pacing control unit is in communication with the pacing database, and wherein the pacing control unit is further configured to determine the pacing information from the pacing data, and wherein the pacing information includes a distance to a surface of the item to be disinfected, a time of UV light illumination of the surface, a rate at which the wand assembly is to be moved in relation to the item to be disinfected, a pacing audio signal providing one or more audio cues that allow the user to synchronize the rate at which the wand assembly is to be moved in relation to the item to be disinfected, and an audio feedback for such rate of the movement.

2. The UV light pacing system of claim 1, wherein the user device comprises a display, wherein the pacing information further includes instructions for operating the wand assembly to disinfect the item to be disinfected, and wherein the instructions are shown on the display.

3. The UV light pacing system of claim 2, wherein the user device further comprises a speaker configured to broadcast the pacing.

4. The UV light pacing system of claim 1, wherein the user device is a handheld device.

5. The UV light pacing system of claim 1, wherein the user device includes the pacing control unit.

6. The UV light pacing system of claim 1, wherein the user device includes the pacing database.

7. The UV light pacing system of claim 1, wherein the user device comprises a display, and wherein the pacing control unit is configured to show a pacing menu screen on the display.

8. The UV light pacing system of claim 7, wherein the pacing menu screen shows one or more training options.

9. The UV light pacing system of claim 1, wherein the item to be disinfected comprises a passenger seat, a monument, a stowage bin assembly, a component within a lavatory, a component within a galley, or a component within a flight deck.

10. The UV light pacing system of claim 1, wherein the UV lamp is configured to emit the UV light having a wavelength between 200 nm-230 nm.

11. The UV light pacing system of claim 1, wherein the UV lamp is configured to emit the UV light having a wavelength of 222 nm.

12. The UV light pacing system of claim 1, wherein the UV lamp is configured to emit the UV light having a wavelength of 230 nm-280 nm.

13. The UV light pacing system of claim 1, wherein the UV lamp is configured to emit the UV light having a wavelength of 254 nm.

14. The UV light pacing system of claim 1, wherein a series of audio files comprise the one or more audio cues, the series of audio files configured to provide voice instructions and pacing for an area of the item to be disinfected.

15. An ultraviolet (UV) light pacing method for a UV light pacing system, the UV light pacing system comprising:
a backpack assembly;
a wand assembly removably coupled to the backpack assembly, the wand assembly including:
a sanitizing head containing a UV lamp that is configured to emit UV light; and
an elongate handle connected to the sanitizing head via a coupler, wherein the coupler allows selective pivoting of the elongate handle relative to the sanitizing head into a first position in which the elongate handle is pivoted toward the sanitizing head for coupling the wand assembly onto the backpack assembly, and into a second position in which the elongate handle is pivoted away from the sanitizing head for extending the length of the wand assembly when the wand assembly is removed from the backpack assembly for sanitizing purposes;
a user device configured to allow a user to select an item to be disinfected with the UV light;

a pacing control unit in communication with the user device, wherein the pacing control unit is configured to output a pacing signal to the user device, wherein the pacing signal includes pacing information regarding operation of the wand assembly to disinfect the item to be disinfected; and
a pacing database configured to store pacing data regarding the item to be disinfected, wherein the pacing control unit is in communication with the pacing database, and wherein the pacing control unit is further configured to determine the pacing information from the pacing data,
wherein the pacing information includes a distance to a surface of the item to be disinfected, a time of the UV light illumination of the surface, a rate at which the wand assembly is to be moved in relation to the item to be disinfected, a pacing audio signal providing one or more audio cues that allow the user to synchronize the rate at which the wand assembly is to be moved in relation to the item to be disinfected, and an audio feedback for such rate of the movement,
the method comprising:
using the wand assembly including the UV lamp to emit the UV light;
selecting, by the user device, the item to be disinfected with the UV light; and
outputting, from the pacing control unit in communication with the user device, the pacing signal to the user device.

16. The UV light pacing method of claim 15, wherein the pacing information further includes instructions for operating the wand assembly to disinfect the item to be disinfected, and wherein the method further comprises showing the instructions on a display of the user device.

17. The UV light pacing method of claim 15, wherein the method further comprises broadcasting the one or more audio cues by a speaker of the user device.

18. The UV light pacing method of claim 15, further comprising showing, by the pacing control unit, a pacing menu screen on a display.

19. The UV light pacing method of claim 18, wherein said showing comprises showing one or more training options.

20. The UV light pacing method of claim 15, wherein said using comprises operating the UV lamp to emit the UV light having a wavelength between 200 nm-230 nm.

21. The UV light pacing method of claim 15, wherein said using comprises operating the UV lamp to emit the UV light having a wavelength of 222 nm.

22. The UV light pacing method of claim 15, wherein said using comprises operating the UV lamp to emit the UV light having a wavelength between 230 nm-280 nm.

23. The UV light pacing method of claim 15, wherein said using comprises operating the UV lamp to emit the UV light having a wavelength of 254 nm.

24. An ultraviolet (UV) light pacing system, comprising:
a backpack assembly;
a wand assembly removably coupled to the backpack assembly, the wand assembly including:
a sanitizing head containing a UV lamp that is configured to emit UV light; and
an elongate handle connected to the sanitizing head via a coupler, wherein the coupler allows selective pivoting of the elongate handle relative to the sanitizing head into a first position in which the elongate handle is pivoted toward the sanitizing head for coupling the wand assembly onto the backpack assembly, and into a second position in which the elongate handle is pivoted away from the sanitizing head for extending the length of the wand assembly when the wand assembly is removed from the backpack assembly for sanitizing purposes;

a user device configured to allow a user to select an item to be disinfected with the UV light, wherein the user device comprises a display and a speaker;

a pacing database that stores pacing data regarding the item to be disinfected; and a pacing control unit in communication with the user device and the pacing database, wherein the pacing control unit is configured to determine the pacing information from the pacing data, wherein the pacing control unit is configured to output a pacing signal to the user device, wherein the pacing signal includes pacing information regarding operation of the wand assembly to disinfect the item to be disinfected, and wherein the pacing information includes:

a distance to a surface of the item to be disinfected;

a time of UV light illumination of the surface;

a rate at which the wand assembly is moved in relation to the item to be disinfected;

instructions for operating the wand assembly to disinfect the item to be disinfected, and wherein the instructions are shown on the display of the user device; and a pacing audio signal providing one or more audio cues that allow the user to synchronize the rate at which the wand assembly is to be moved in relation to the item to be disinfected, and an audio feedback for such rate of the movement, and wherein the one or more audio cues are broadcast by the speaker of the user device.

25. The UV light pacing system of claim 24, wherein a series of audio files comprise the one or more audio cues, the series of audio files configured to provide voice instructions and pacing for an area of the item to be disinfected.

* * * * *